United States Patent
Freed et al.

(10) Patent No.: US 8,522,839 B2
(45) Date of Patent: Sep. 3, 2013

(54) ADAPTERS FOR USE WITH AN ANESTHETIC VAPORIZER

(75) Inventors: Simon Freed, Hillsborough, NJ (US); Michael R. Prisco, Geneva, IL (US); Eric Hyman, Grafton, MA (US); Raymond D. Clark, Valley Center, CA (US); Alan W. Marttila, Waukegan, IL (US); John DePiano, Burlington, MA (US); Richard P. Meyst, Valley Center, CA (US); Timothy B. Meluch, Grayslake, IL (US); David Chesley, Duxbury, MA (US); Roy T. Henderson, Escondido, CA (US)

(73) Assignees: Baxter International Inc., Deerfield, IL (US); Baxter Healthcare SA, Glattpark (Opikon) (CH)

( * ) Notice: Subject to any disclaimer, the term of this patent is extended or adjusted under 35 U.S.C. 154(b) by 1418 days.

(21) Appl. No.: 11/437,904

(22) Filed: May 19, 2006

(65) Prior Publication Data

US 2007/0204931 A1 Sep. 6, 2007

Related U.S. Application Data

(60) Provisional application No. 60/779,466, filed on Mar. 6, 2006, provisional application No. 60/788,517, filed on Mar. 31, 2006.

(51) Int. Cl.
*B65B 1/04* (2006.01)
(52) U.S. Cl.
USPC ............ 141/353; 141/349; 141/366; 141/383

(58) Field of Classification Search
USPC ................ 141/346–349, 351–353, 363–366, 141/382–385
See application file for complete search history.

(56) References Cited

U.S. PATENT DOCUMENTS

| | | | |
|---|---|---|---|
| 3,416,577 A | 12/1968 | Franz | |
| 4,625,779 A | 12/1986 | Ryschka et al. | |
| 4,693,853 A | 9/1987 | Falb et al. | |
| 4,825,860 A | 5/1989 | Falb et al. | |
| 4,862,918 A | 9/1989 | Schroeder | |
| 4,867,212 A | 9/1989 | Mohr et al. | |
| 4,879,997 A | 11/1989 | Bickford | |
| 4,883,049 A | 11/1989 | McDonald | |
| 4,893,659 A | 1/1990 | Loliger | |
| 4,932,398 A | 6/1990 | Lancaster et al. | |

(Continued)

FOREIGN PATENT DOCUMENTS

| EP | 0 678 042 B1 | 6/2000 |
|---|---|---|
| WO | WO 96/06301 | 2/1996 |

OTHER PUBLICATIONS

International Search Report and Written Opinion for International application No. PCT/US2007/062855, dated Oct. 10, 2007.

*Primary Examiner* — Jason K Niesz
(74) *Attorney, Agent, or Firm* — Marshall, Gerstein & Borun LLP

(57) ABSTRACT

Adapters are provided for establishing fluid communication between an anesthetic agent container and an anesthetic vaporizer having a fluid port. The adapter may be mountable on the vaporizer to cooperate with the spout of an anesthetic agent container or may be mountable on an anesthetic agent container to cooperate with the fluid port of an anesthetic vaporizer to provide a sealing and/or retaining relationship therebetween.

7 Claims, 26 Drawing Sheets

(56) References Cited

U.S. PATENT DOCUMENTS

| | | | |
|---|---|---|---|
| 5,048,874 A | 9/1991 | Ohlsson | |
| 5,144,984 A | 9/1992 | Westerberg et al. | |
| 5,144,991 A | 9/1992 | Wallroth et al. | |
| 5,170,823 A | 12/1992 | Gregory et al. | |
| 5,287,898 A | 2/1994 | Falb et al. | |
| 5,381,836 A * | 1/1995 | Braatz et al. | 141/21 |
| 5,419,316 A | 5/1995 | Bernstein | |
| 5,427,145 A | 6/1995 | Grabenkort | |
| 5,474,112 A | 12/1995 | Carola | |
| 5,478,506 A | 12/1995 | Lavimodiere | |
| 5,505,236 A | 4/1996 | Grabenkort et al. | |
| 5,536,047 A | 7/1996 | Detable et al. | |
| 5,585,045 A | 12/1996 | Heinonen et al. | |
| 5,617,906 A | 4/1997 | Braatz et al. | |
| 5,653,475 A | 8/1997 | Scheyhing et al. | |
| 5,682,874 A | 11/1997 | Grabenkort et al. | |
| 5,687,777 A | 11/1997 | Dobson et al. | |
| 5,740,835 A * | 4/1998 | Murphy | 137/614.05 |
| 5,758,640 A | 6/1998 | Kamppari et al. | |
| 5,810,001 A | 9/1998 | Genga et al. | |
| 5,839,487 A | 11/1998 | Moll et al. | |
| 5,911,250 A | 6/1999 | Turker et al. | |
| 5,915,427 A | 6/1999 | Grabenkort | |
| 5,983,964 A * | 11/1999 | Zielinksi et al. | 141/346 |
| 6,125,893 A | 10/2000 | Braatz et al. | |
| 6,149,206 A | 11/2000 | DiRocco | |
| 6,231,084 B1 | 5/2001 | Hester et al. | |
| 6,371,528 B1 | 4/2002 | Kimura | |
| 6,394,087 B1 | 5/2002 | Kankkunen et al. | |
| 6,585,016 B1 | 7/2003 | Falligant et al. | |
| 6,637,725 B2 * | 10/2003 | Davis et al. | 251/149.6 |
| 6,672,306 B2 | 1/2004 | Loser et al. | |
| 6,676,172 B2 | 1/2004 | Alksnis | |
| 6,745,765 B2 | 6/2004 | Kullik et al. | |
| 6,745,800 B1 | 6/2004 | Sansom | |
| 6,789,698 B2 | 9/2004 | Gloor et al. | |
| 6,817,390 B2 | 11/2004 | Falligant et al. | |
| 6,929,041 B2 | 8/2005 | Falligant et al. | |
| 6,948,642 B2 | 9/2005 | Awad | |
| 7,290,571 B2 * | 11/2007 | Bunke et al. | 141/18 |
| 2003/0075241 A1 | 4/2003 | Videbrink | |

* cited by examiner

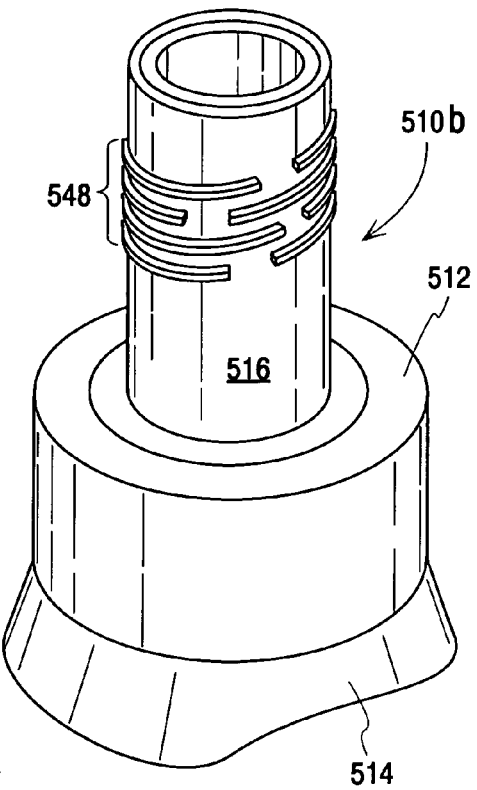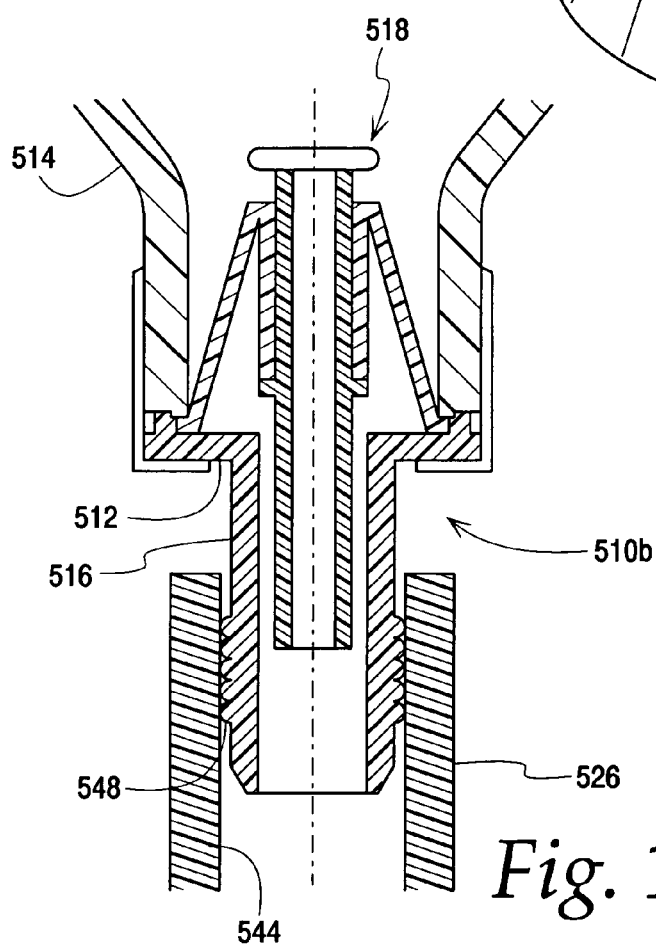
Fig. 16A
Fig. 16B

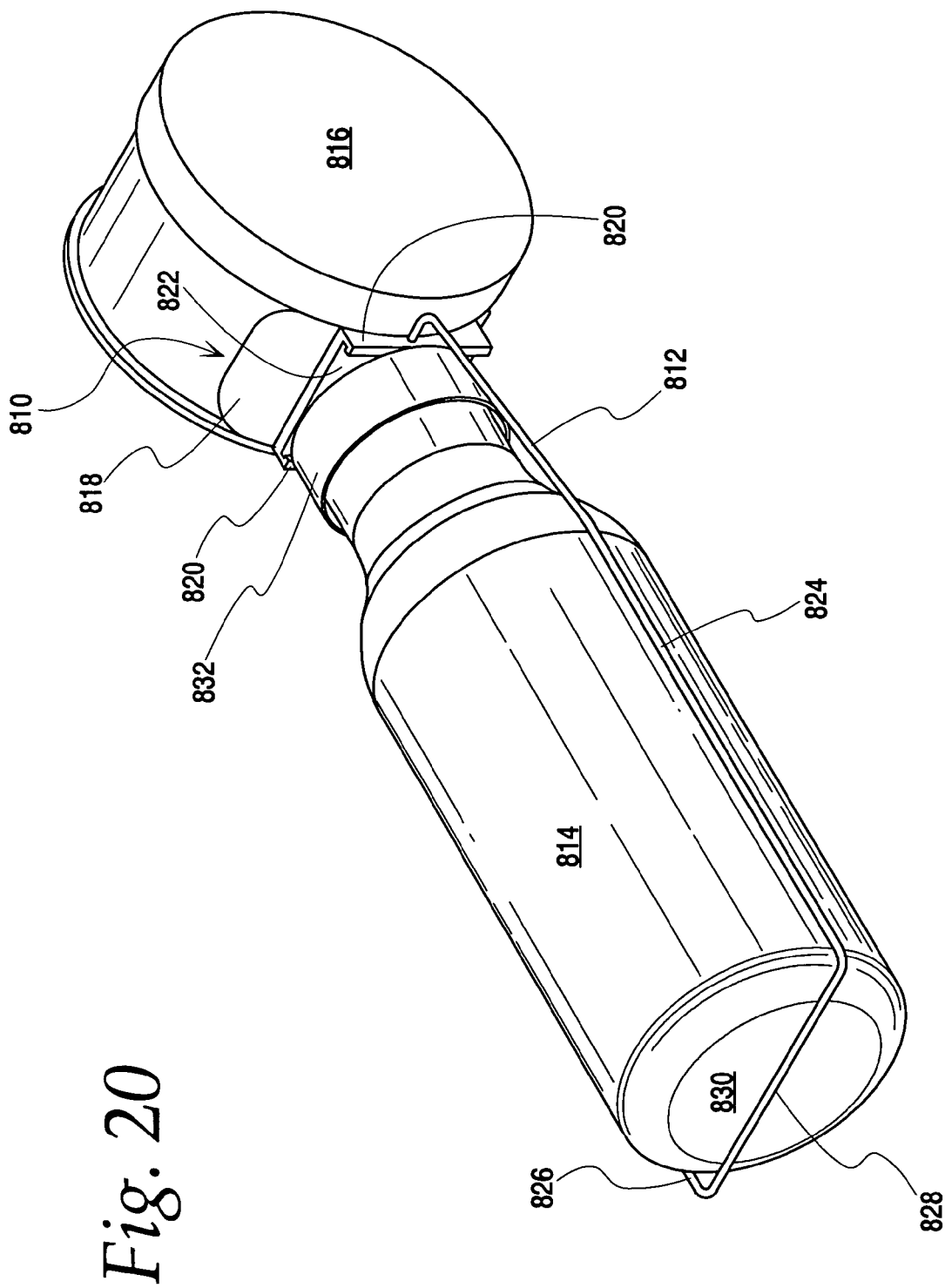

ADAPTERS FOR USE WITH AN ANESTHETIC VAPORIZER

CROSS REFERENCE TO RELATED APPLICATIONS

This application claims priority from and the benefit of provisional patent application Ser. No. 60/779,466, filed Mar. 6, 2006, and provisional patent application Ser. No. 60/788,517, filed Mar. 31, 2006, both of which are hereby incorporated herein by reference.

BACKGROUND

1. Field of the Disclosure

This disclosure generally relates to apparatus for allowing selective fluid communication between an anesthetic agent container and an anesthetic vaporizer. More particularly, the disclosure relates to an adapter mountable on an anesthetic agent container or on an anesthetic vaporizer for facilitating fluid transfer therebetween.

2. Description of Related Art

During surgical procedures, it often is necessary to anesthetize a patient. One method of delivering anesthetic is in a gaseous form, which is inhaled by the patient. For the safety of the patient and medical personnel, the anesthetic agent is typically transported in liquid form in a suitable container. Known liquid anesthetics include halothane, isoflurane, sevoflurane, desflurane, enflurane, and methoxyflurane. The liquid anesthetic is ultimately dispensed into an anesthetic vaporizer, which mixes the liquid anesthetic agent with a carrier gas, such as oxygen or nitrous oxide, that is inhalable by a patient.

Liquid anesthetics are relatively volatile and can evaporate at room temperature. Before it can be used, the anesthetic agent must be transferred from a first closed environment, e.g., a container or bottle, to a second closed environment, e.g., a vaporizer. In order to transfer the anesthetic, it is well-known to provide a vaporizer fluid port with a valving system that is selectively openable to allow a liquid anesthetic agent to be poured into an internal sump of the vaporizer. Such valving systems are described in U.S. Pat. Nos. 5,381,836 and 5,617,906 to Braatz et al., which are hereby incorporated herein by reference. The valving systems described in Braatz et al. are suitable for use with, for example, commercial desflurane vaporizers. Examples of commercial vaporizers include, but are not limited to the Tec 6 Plus™ of Datex-Ohmeda, Inc. and the D-Vapor™ or Devapor® of Drager Medical AG & Co. KG.

The above patents describe an arrangement in which the anesthetic agent container is provided with an integral or separate adapter with a valving system configured to mate with the vaporizer valving system and allow for selective dispensing of the liquid anesthetic contained therein. To transfer anesthetic agent from the container to the vaporizer, the adapter is inserted into the vaporizer fluid port. As a result of contact between spring-biased portions of the adapter and vaporizer valving systems, fluid communication between the container and vaporizer is opened and fluid exchange can commence.

Some commercial vaporizers include a stop cock or similar means for preventing fluid transfer even after the adapter is engaged by the vaporizer and both valves are opened. In such vaporizers, the stop cock is typically opened by rotating the engaged adapter from a down position to an up position, as described by Braatz et al. In the up position, the stop cock is open and liquid anesthetic agent is allowed to flow from the container into the vaporizer. Thereafter, the adapter is rotated to the down position, if necessary, and removed from the vaporizer fluid port, which automatically closes both valves.

The filling systems of Braatz et al. disclose a sealing surface that is provided toward a free end of the outlet of an adapter associated with an anesthetic agent container. The sealing surface forms a seal with a vaporizer inlet in order to prevent leakage while the adapter is engaged by the vaporizer and one or both of the valves are open. A typical adapter according to Braatz et al. has a tubular spout with a free end that is encircled by an elastomeric o-ring seated in a groove or channel of the spout. The spout is inserted into the fluid port of the vaporizer and the o-ring deforms to form a fluid seal between the outer surface of the spout and an inner surface of the fluid port.

Another characteristic of the filling systems of Braatz et al. is that they use a generally annular projection on the adapter spout as a means for preventing accidental disengagement of an engaged adapter from the vaporizer. Vaporizers requiring rotation of an engaged adapter to open a stop cock typically include a curved slot with a key-hole opening to receive the adapter in the down position. Rotation of the adapter along the slot to the up position causes the slot to grip the projection, thereby preventing disengagement. The projection-slot configuration prevents disengagement of the adapter in any position other than through the key-hole opening of the down position.

As set forth in more detail below, the present disclosure sets forth an improved adapter embodying advantageous alternatives to the sealing and/or retention systems of prior art devices.

SUMMARY

In general, the present disclosure is directed to adapters for establishing fluid communication between an anesthetic agent container and an anesthetic vaporizer having a fluid port. More particularly, the present disclosure sets forth an adapter for creating a sealing and/or a retaining relationship between an anesthetic vaporizer and an engaged anesthetic agent container. As described in more detail below, sealing and/or retaining may be accomplished in several different ways. Thus, for example, a base of the adapter is securable to the vaporizer and surrounds a fluid port of the vaporizer. A sidewall extends upwardly from the base to an upper end having a sealing lip, which is generally coaxial with the fluid port when the adapter is in engagement with the vaporizer. The sealing lip is adapted for sealing engagement with an anesthetic agent container when at least a portion of the same is inserted into the adapter.

In another example, an adapter has a base and a valved, generally tubular spout extending away from the base.

A sealing member of the adapter is adapted for sealing engagement with an upper lip of the fluid port of an anesthetic vaporizer when at least a portion of the spout is inserted into the fluid port.

In another example, an adapter has a generally tubular spout with an end lip at a first end of the spout and a collar spaced from the first end of the spout. A radially expandable member is disposed between the end lip and the collar. The collar is movable along the spout by an actuator.

In another example, an adapter is provided with a base and a valved, generally tubular spout. The spout includes an upper end which has a substantially continuous outer radius and is adapted to be received by a fluid port of an anesthetic vapor.

In accordance with another example, an adapter has a base and a valved, generally tubular spout extending away from the base. A retainer associated with the spout or with an adapter valve assembly is adapted for engagement with a central pin or a fluid port of a vaporizer when at least a portion of the spout is inserted into the fluid port of the vaporizer.

In accordance with yet another example, an adapter has a base and a valved, generally tubular spout extending away from the base. The outer surface of the spout includes a non-continuous sealing member adapted for sealing engagement with the fluid port of an anesthetic vaporizer when at least a portion of the spout is inserted into the fluid port.

In another example, an adapter has a base and a valved, generally tubular spout extending away from the base. An upper end of the spout is adapted to be received by the fluid port of an anesthetic vaporizer for sealing engagement with at least an upper portion of the fluid port.

In another example, an adapter has a base and a valved, generally tubular spout extending away from the base. An adapter valve assembly is retractable to radially expand at least a portion of the spout.

In accordance with yet another example, an adapter has a base and a valved, generally tubular spout extending away from the base. An adapter valve assembly includes a sealing member adapted for sealing engagement with a central pin of a vaporizer valve assembly when at least a portion of the spout is inserted into the fluid port of an anesthetic vaporizer.

In still another example, an adapter has a base and a generally tubular spout extending away from the base. The spout is movable with respect to the base to allow fluid flow through the spout.

In accordance with another example, a base of an adapter is securable to a vaporizer and surrounds a fluid port of the vaporizer. A pivoting retainer is associated with the sidewall and configured to pivot with respect to the same. The pivoting retainer is movable to engage and retain a portion of an anesthetic agent container when the anesthetic agent container is received by the fluid port.

In accordance with another example, a retention system includes a generally tubular spout associable with an anesthetic agent container and an adapter with a base securable to a vaporizer. The adapter is configured to surround a fluid port of the vaporizer and is adapted to receive at least a portion of the spout. A sidewall extends upwardly from the base to an upper end having an aperture for receiving at least a portion of the spout. A slot is associated with the aperture for receiving the retaining post as the spout is inserted into the adapter. A pocket associated with the slot is spaced below the upper end, such that a spout received by the adapter is rotatable to move the retaining post into the pocket.

In another example, an adapter has a base and a generally tubular spout extending away from the base. An adapter valve assembly controls fluid flow through the spout. A generally annular shielding member is associated with at least one of the spout and the base. The shielding member has a maximum diameter that is larger than an inner diameter of an upper lip of a vaporizer fluid port. When the spout is fully inserted into the fluid port, the shielding member is spaced from the upper lip.

In accordance with another example, an adapter has a base and a generally tubular spout extending away from the base to a distal end. A sealing membrane and at least one spout through hole are associated with the distal end. A valve disk is also associated with the distal end and rotatable with respect to the same. The valve disk includes a central opening in alignment with the sealing membrane and at least one disk through hole. The valve disk is rotatable to bring the spout through hole into alignment with the disk through hole.

Adapters generally described above provide an effective sealing and/or retention mechanism between an anesthetic vaporizer and an anesthetic agent container. The adapters described herein are particularly well-suited for connecting a container housing an amount of an anesthetic agent, including volatile agents such as, but not limited to, desflurane to a corresponding vaporizer. Of course, it will be appreciated that the adapters described herein are not limited to particular medical devices or anesthetic agents.

BRIEF DESCRIPTION OF THE DRAWINGS

FIG. 16A is a front perspective view of yet another embodiment of an adapter with a non-continuous sealing member;

FIG. 16B is a cross-sectional view of the adapter of FIG. 16A, received in part by a fluid port of an anesthetic vaporizer;

FIG. 20 is a front perspective view of an adapter having a pivoting retainer in engagement with an anesthetic agent container;

DESCRIPTION OF THE PREFERRED EMBODIMENTS

It will be understood that the disclosed embodiments generally described below and illustrated in the attached drawings are merely exemplary of the present invention, which may be embodied in various forms. Therefore, specific details disclosed herein are not to be interpreted as limiting, but rather as representative and provide a basis for variously employing the present invention in any appropriate manner understood by one of ordinary skill in the art.

All aspects of the adapters described herein and, in particular, the illustrated embodiments which follow may be adapted to cooperate with conventional anesthetic vaporizers, anesthetic agent containers, and valving systems.

Figure 1:
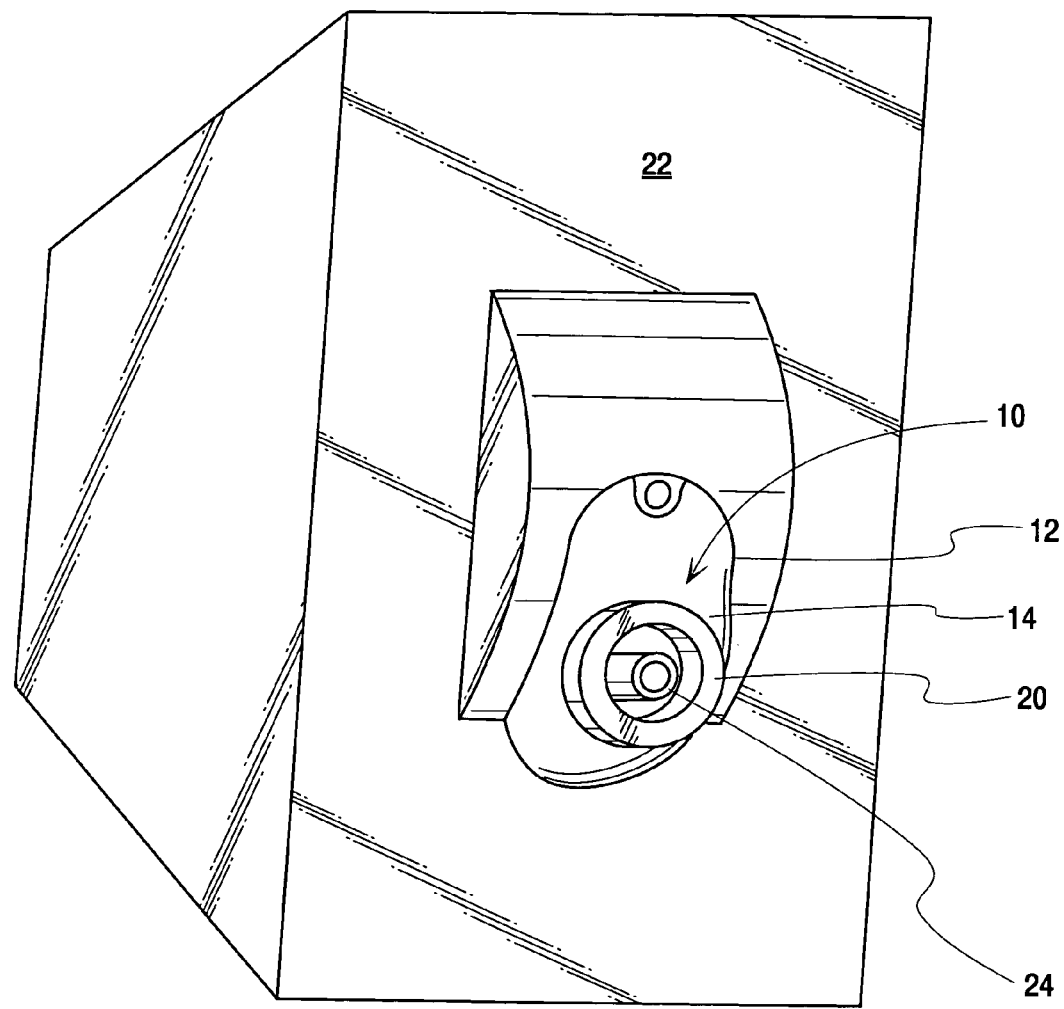
FIG. 1 is a front perspective view of a sealing adapter mounted on an anesthetic vaporizer.
Figure 2:
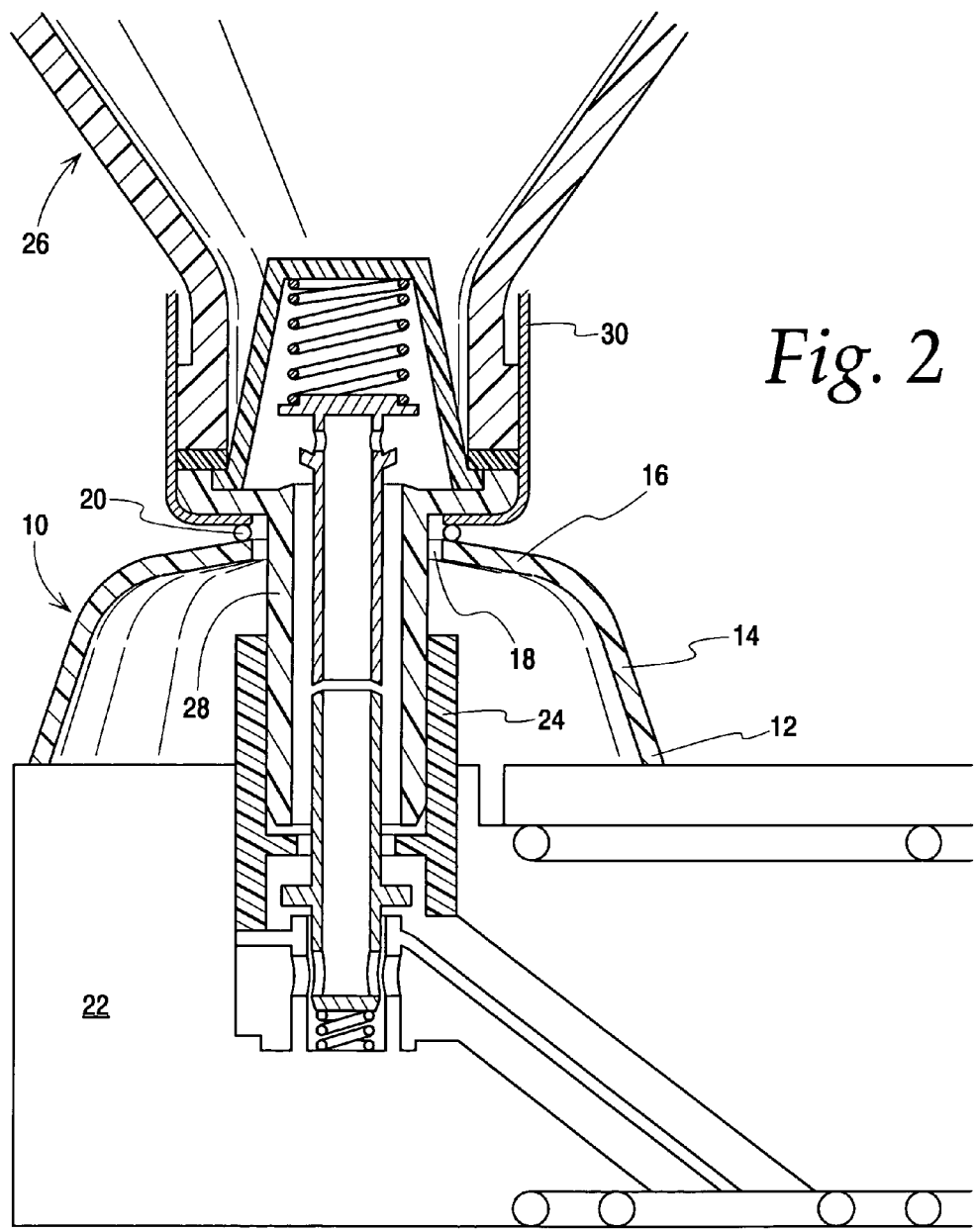
FIG. 2 is a cross-sectional view of an engaged adapter and vaporizer according to the embodiment of FIG. 1.

FIGS. 1 and 2 show an adapter according to an aspect of the present invention. The adapter is generally identified as element 10 in FIGS. 1 and 2. Adapter 10 will typically include a base 12 and a sidewall 14 extending away or upwardly from the base 12 to an upper end 16. The upper end 16 defines an opening 18 generally encircled by a sealing lip 20. The sidewall 14 is preferably substantially comprised of a plastic or elastomeric material. The sidewall 14 may also be substantially comprised of a stainless material, such as stainless steel. The sealing lip 20 is preferably substantially comprised of an elastomeric material.

In one embodiment, the adapter 10 is mountable on a vaporizer 22 having a valved fluid port 24 suitable for receiving at least a portion of a valved anesthetic agent container 26. As illustrated in FIGS. 1 and 2, the fluid port 24 is substantially contained within a shroud defined by the adapter 10 and is accessible only via the adapter opening 18. Preferably, the adapter 10 is mechanically fastened to the vaporizer 22 using screws or the like and aligned such that the opening 18 is generally coaxial with the fluid port 24. If the fluid port 24 is configured to be movable with respect to the vaporizer 22, e.g., rotatable between a down position and an up position as described by Braatz et al., then the adapter 10 may be preferably mounted for movement with the fluid port 24.

In the embodiment where the adapter 10 is mounted on the vaporizer 22, during attachment of the valved anesthetic agent container 26 to the vaporizer 22, a spout 28 of the container 26 is aligned with the opening 18 and inserted into the fluid port 24. A portion of the container 26, such as the spout 28 or, as illustrated in FIG. 2, a ferrule 30 contacts the sealing lip 20 of the adapter 10 to form a fluid seal therewith. When used herein, the term "fluid seal" is used generally to describe any seal that substantially prevents the escape of a fluid. As such, it may incorporate a liquid seal and/or a vapor seal.

Preferably, the fluid seal is formed before fluid communication between the container 26 and the vaporizer 22 is established. Hence, it will be seen that the adapter 10 provides a fluid seal without the use of an o-ring of known devices. Of course, the adapter 10 may be used in conjunction with a container having an o-ring in order to create an auxiliary fluid seal between the container and the vaporizer.

Figure 4:
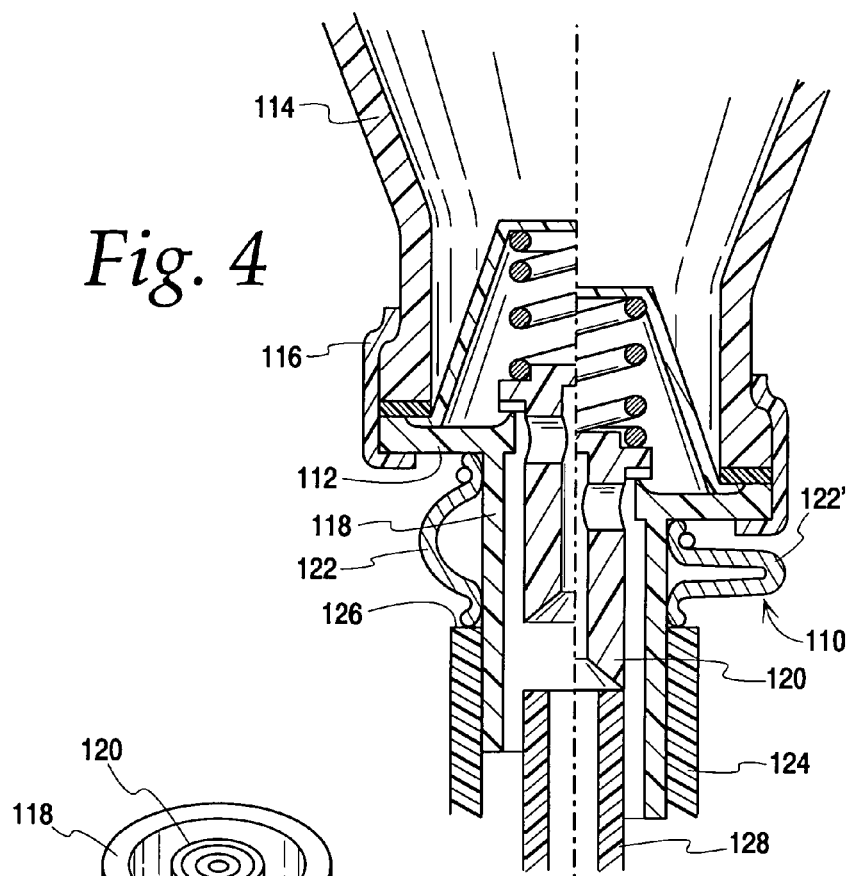
FIG. 4 is a split view of a cross-section of an adapter according to the embodiment of FIG. 3, received in part by a fluid port of an anesthetic vaporizer.
Figure 3:
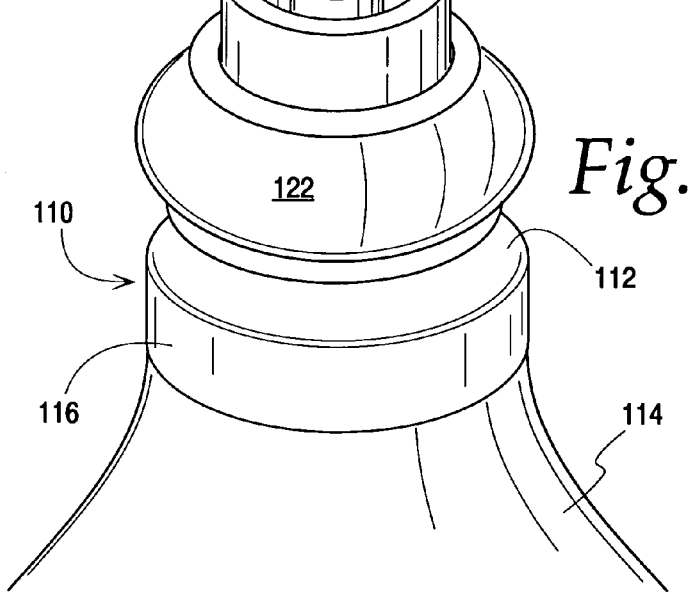
FIG. 3 is a front perspective view of an adapter with a sealing member mounted on an anesthetic agent container.

FIGS. 3 and 4 illustrate another aspect of the present invention, which may be practiced alone or in combination with the adapter 10 of FIGS. 1 and 2, as will be described herein. An adapter 110 includes a base 112 mountable on an anesthetic agent container 114 containing an amount of anesthetic agent. The base 112 may be mounted on the container 114 by any suitable means, such as by a screw cap or, as illustrated in FIGS. 3 and 4, a ferrule 116. A generally tubular spout 118 is preferably formed integrally with the base 112 and extends away from the same. An adapter valve assembly 120 is associated with the spout 118 for controlling fluid flow therethrough. The exact configuration of the adapter valve assembly 120 is not critical and may vary according to the type of anesthetic agent within the container 114, the valving system of the vaporizer to which the container 114 will be connected, and other factors. For example, in the case of an adapter 110 intended to transfer a volatile anesthetic agent such as desflurane from a container to a vaporizer, the adapter valve assembly 120 may preferably take the form of the valving system of U.S. Pat. Nos. 5,381,836 and 5,617,906 to Braatz et al., previously incorporated by reference.

In the embodiment illustrated in FIGS. 3 and 4, a sealing member 122 encircles and is secured to the spout 118 by any of a number of known methods. For example, the sealing member 122 may be adhesively bonded to the spout 118 or heat sealed thereto. Of course, a suitable sealing mechanism will depend on the materials to be joined and other factors, but such a selection is well within the capacity of one having ordinary skill in the art. If the spout 118 is provided with an annular projection or locking ring, not illustrated, suitable for use with the prior art key-hole retention system described above, then it may be convenient to attach the sealing member 122 to an upper surface of the projection.

The sealing member 122 is preferably substantially comprised of a deformable and/or elastomeric material. Examples of suitable materials include, but are not limited to, silicone, neoprene, and rubber (synthetic and/or natural). The sealing member 122 may by configured to axially foreshorten under an axial load. For example, FIG. 4 shows that the illustrated undulating configuration allows the sealing member 122 to deform into an axially foreshortened or compressed condition 122' as the spout 118 is further advanced into a vaporizer fluid port 124. As shown in FIG. 4, movement of the adapter spout 118 into the vaporizer fluid port 124, places the sealing member 122 in contact with an upper lip 126 of the fluid port 124 to create a fluid seal. When used herein to describe the fluid port, the term "upper lip" refers to the distal or outer end of the fluid port, which is spaced away from the associated vaporizer. Preferably, the fluid seal is formed prior to establishment of fluid communication between the container 114 and a vaporizer being established. If the sealing member 122 is axially compressible, then it allows the spout 118 to be further inserted into the fluid port 124 after the seal has been formed. Hence, the sealing member 122 of FIG. 4 initially contacts the upper lip 126 and forms a fluid seal, then is deformed to the compressed condition 122' as the spout 118 is further advanced into the fluid port 124, and finally the adapter valve assembly 120 contacts a vaporizer valve assembly 128 to allow fluid communication.

While the use of the adapter 110 has been described and illustrated with regard to a fluid port 124, it will be appreciated that the adapter 110 can also be used with the adapter 10 of FIGS. 1 and 2, wherein the sealing member 122 contacts and forms a fluid seal with the sealing lip 20 instead of, or in addition to, the upper end 16 of the adapter 10.

Figure 5:
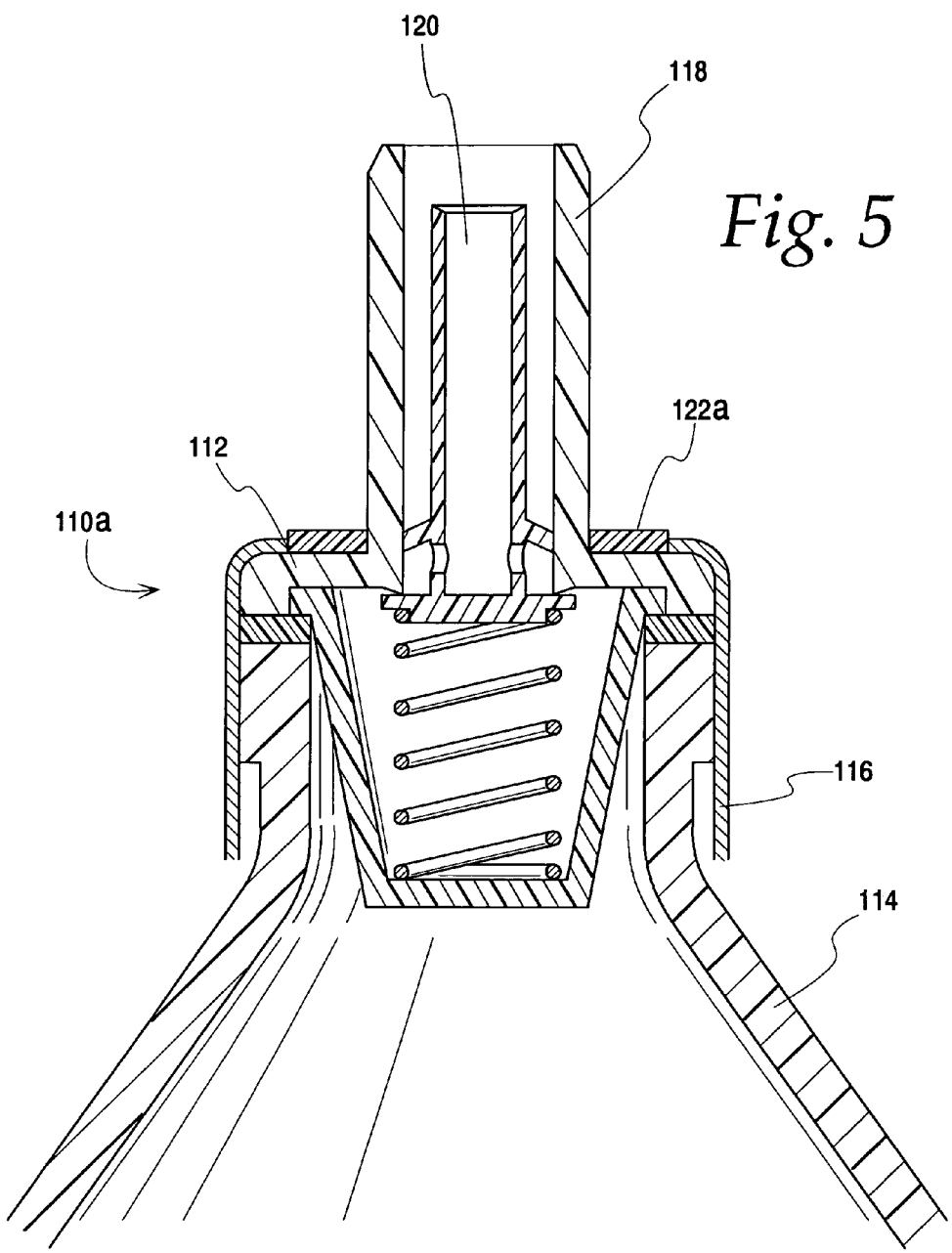
FIG. 5 is a cross-sectional view of an adapter having an alternative embodiment of the sealing member illustrated in FIG. 3.

FIG. 5 shows an alternative embodiment of the adapter of FIGS. 3 and 4. In general, the adapter 110a operates according to the above description of adapter 110 of FIGS. 3 and 4. However, as shown in FIG. 5, a sealing member 122a is secured to the base 112 instead of to the spout 118. The embodiment of FIG. 5 may be preferred, because the sealing member 122a may be secured to the base 112 by the same ferrule 116 used to secure the base 112 to the container 114. In the embodiment of FIG. 5, the sealing member 122a is illustrated as a disk or ring made of foam or some other deformable material, but it may take other forms suitable for sealing engagement with the upper lip 126 of the fluid port 124 or a sealing lip 20 of an adapter 10, such as the undulating configuration of FIGS. 3 and 4.

Figure 6:
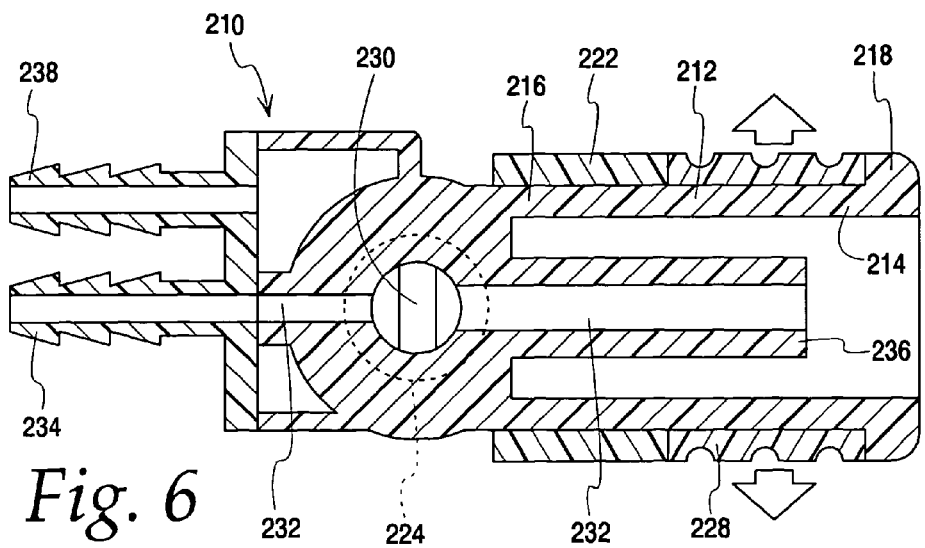
FIG. 6 is a cross-sectional view of an adapter with a radially expandable member according to an aspect of the present invention.
Figure 7A:
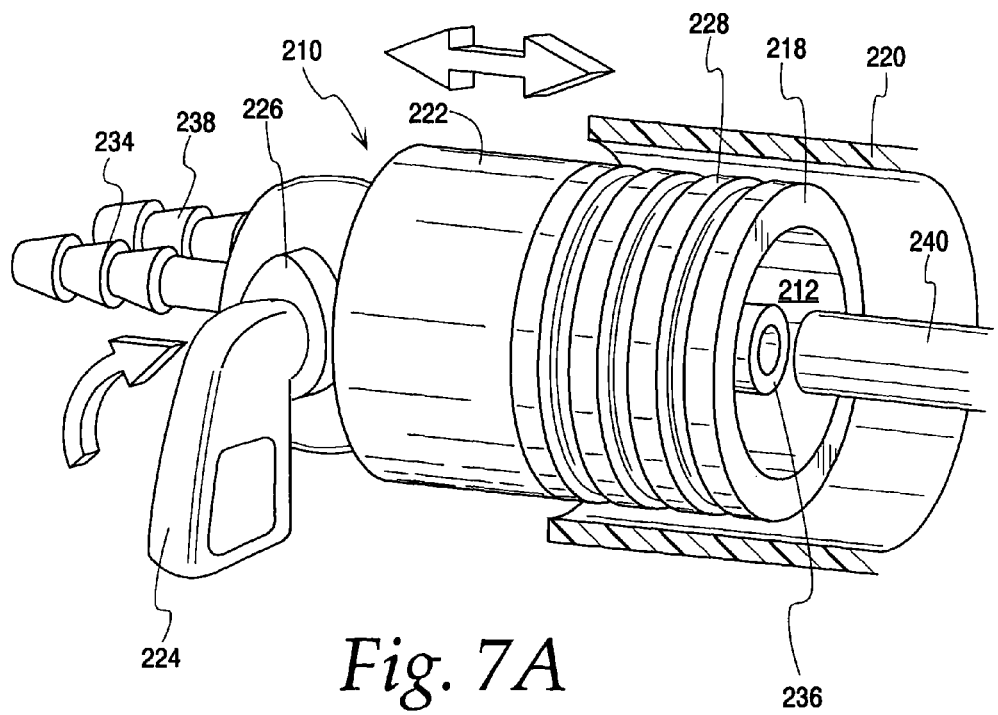
FIG. 7A is a front perspective view of the adapter of FIG. 6, received in part by a fluid port of an anesthetic vaporizer.
Figure 7B:
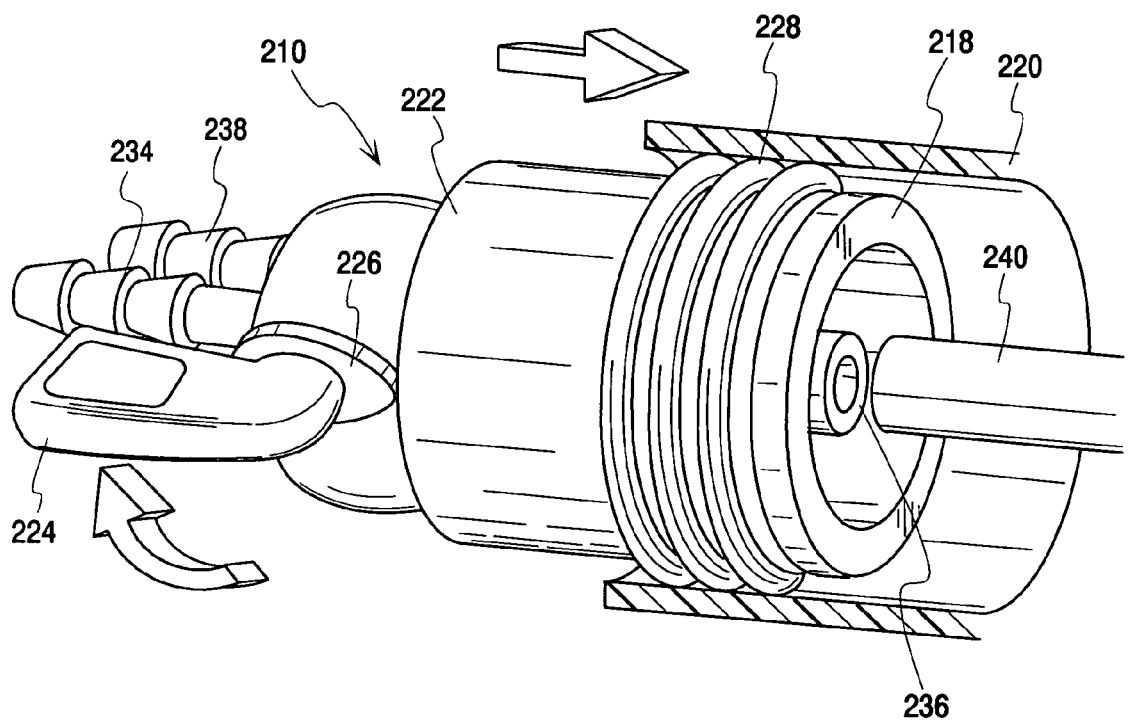
FIG. 7B is a front perspective view of the adapter of FIG. 7A, with the radially expandable member in a radially expanded condition.

FIGS. 6-7B illustrate yet another example of a sealing and/or retaining arrangement. In FIGS. 6-7B, an adapter 210 may include a generally tubular spout 212 extending between a first end 214 and a second end 216. The first end 214 has a generally annular end lip 218 configured to be received by a fluid port 220 of an anesthetic vaporizer. A collar 222 is spaced from the first end 214 and axially movable along the spout 212. The collar 222 is movable by an actuator, which is illustrated in FIGS. 6-7B as a knob 224 associated with the second end 216 of the spout 212. The knob 224 includes an eccentric disk or cam 226 engageable with the collar 222. As shown in FIGS. 7A and 7B, the knob 224 is rotated to cause the cam 226 to move the collar 222 toward the end lip 218. Movement of the collar 222 toward the end lip 218 axially compresses a radially expandable member 228 disposed between the end lip 218 and the collar 222. The radially expandable member 228 expands radially or outwardly away from the spout 212 when it is compressed between the collar 222 and the end lip 218. Preferably, the radially expandable member 228 is substantially comprised of a deformable and/or elastomeric material suitable for the above-described action. The illustrated radially expandable member 228 takes the form of a sheet of pleated material or a bellows.

In addition to moving the collar 222, rotating the knob 224 also rotates an associated valve 230 in the adapter 210. Fluid flow through the adapter 210 is achieved by a lumen 232, principally defined by a first nozzle 234 and a central tube 236. The lumen 232 is also in fluid communication with a second nozzle 238 that is non-coaxial with the spout 212, in contrast to the lumen 232, the first nozzle 234, and the central tube 236. Alternatively, the valve 230 may be provided with a separate lumen, not illustrated, that communicates with the second nozzle 238. In the orientation of FIGS. 6 and 7A, the valve 230 is misaligned with the lumen 232 and flow is prevented. Rotating the knob 224 to the orientation of FIG. 7B rotates the valve 230 into alignment with the lumen 232, thereby allowing fluid flow through the adapter 210. Thus, it will be seen that the same action that expands the radially expandable member 228 also opens fluid flow through the adapter lumen 232.

The adapter 210 is used to connect an anesthetic agent container, not illustrated, to the fluid port 220 of an anesthetic vaporizer for fluid transfer. The container is connected to the first nozzle 234 and the second nozzle 238 by tubing or the like. The separate nozzles allow for the simultaneous flow of one fluid from the container into the vaporizer, typically a liquid anesthetic, and another fluid from the vaporizer to the container, typically a pressurized vapor. Fluid communication between the container and the nozzles 234 and 238 may be regulated by a suitable valve system.

A vaporizer, not illustrated, is connected to the adapter 210 by inserting at least a portion of the adapter 210 into the vaporizer fluid port 220. When the end lip 218 and at least a portion of the radially expandable member 228 are inserted into the fluid port 220 of an anesthetic vaporizer, as shown in FIG. 7A, the central tube 230 of the adapter 210 contacts a vaporizer adapter valve 240 in the fluid port 220 and moves it into an open position. Preferably, the adapter 210 is used with a vaporizer having a stop cock, as described above, to regulate fluid flow after the vaporizer valve has opened. Regardless of the presence or absence of a stop cock, fluid flow between the container and vaporizer in the orientation of FIG. 7A is prevented by misalignment of the valve 230 and the lumen 232. It is preferred that there is no fluid flow through the spout 212 in FIG. 7A, because there is no seal between the adapter 210 and the fluid port 220.

When fluid flow between the container and vaporizer is desired, the knob 224 is rotated into the position of FIG. 7B to move the collar 222 toward the spout end lip 218, thereby expanding the radially expandable member 228 and pressing it against the fluid port 220 to form a sealing arrangement therewith. If preferred, the radially expandable member 228 may be adapted to form a sufficiently tight fit with the fluid port 220 that a retention arrangement, in addition to the previously described sealing arrangement, is established. Rotation of the knob 224 also rotates the valve 230 into alignment with the lumen 232, thereby opening fluid flow through the spout 212. Of course, if the vaporizer includes a stop cock, then it is opened to allow fluid transfer between the container and the vaporizer. Thus, it will be seen that the adapter may allow for a sealed connection between an anesthetic agent container and a vaporizer, without the use of an o-ring of prior art devices.

Figure 8:
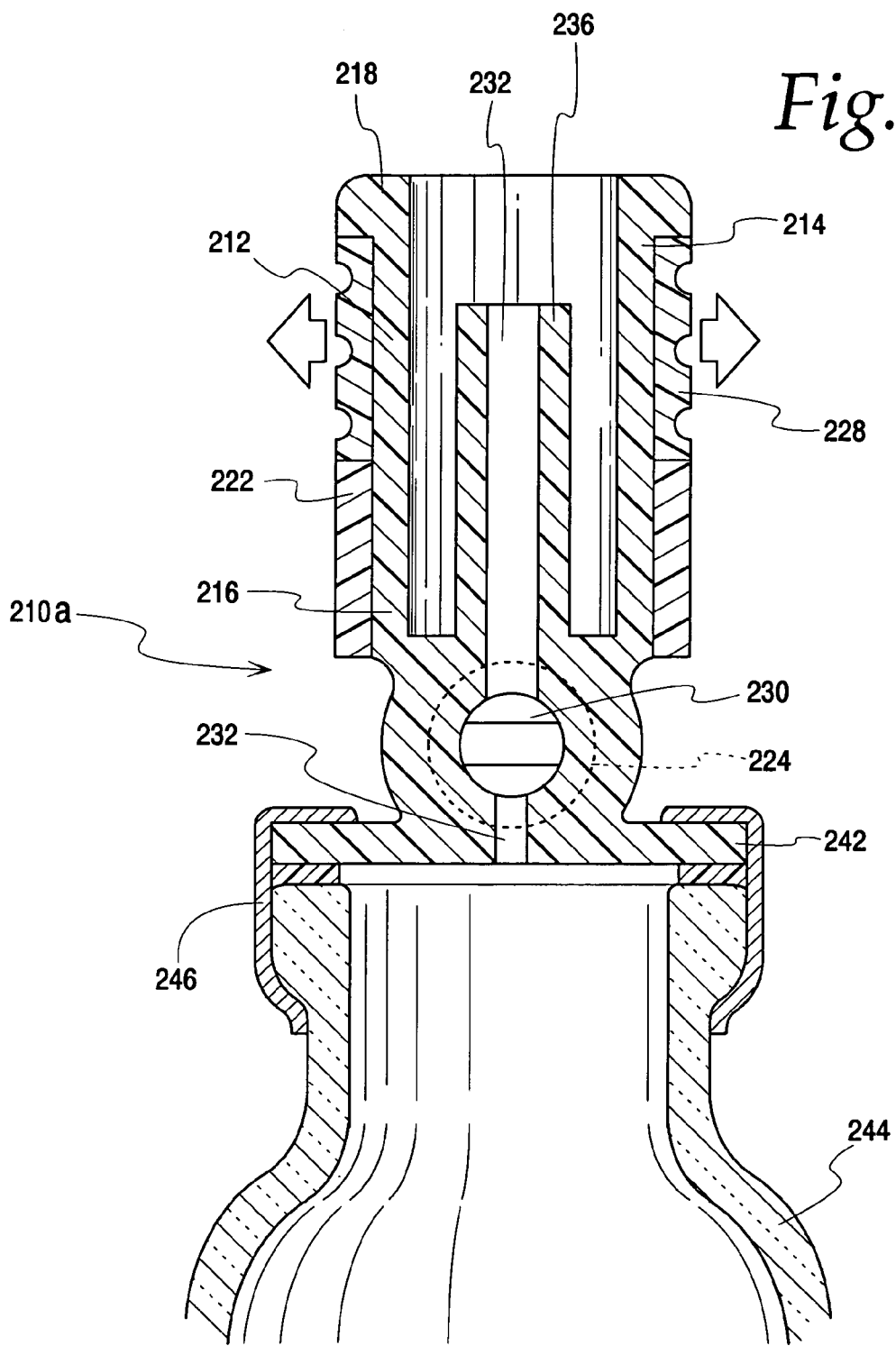
FIG. 8 is a cross-sectional view of an alternative embodiment of an adapter having a radially expandable member mounted on an anesthetic agent container.

FIG. 8 shows an alternative embodiment of the adapter 210 of FIGS. 6-7B. The adapter 210a includes components similar to the adapter 210 of FIGS. 6-7B, except that the nozzles are replaced by a base 242 associated with the second end 216, which is directly mountable on a container 244 housing an amount of an anesthetic agent. The base 242 may be secured to the container 244 by a ferrule 246 or other suitable means, such as a threaded connection. In use, at least a portion of the spout 212 is inserted into a vaporizer fluid port, then the actuator knob 224 is rotated to expand the radially expandable member 228 and to align the valve 230 with the lumen 232, which creates a fluid seal with the fluid port and allows fluid flow through the adapter 210a, respectively. As with the embodiments of FIGS. 6-7B, the valve 230 may be provided with a separate lumen, not illustrated, that allows communication between the container 244 and the spout 212 when the valve 230 is properly aligned. It may be preferred to provide at least two separate fluid flowpaths when transferring an anesthetic agent such as desflurane, because pressurized vapor typically flows from the vaporizer to the container while the liquid anesthetic agent is flowing into the vaporizer.

Figure 9A:
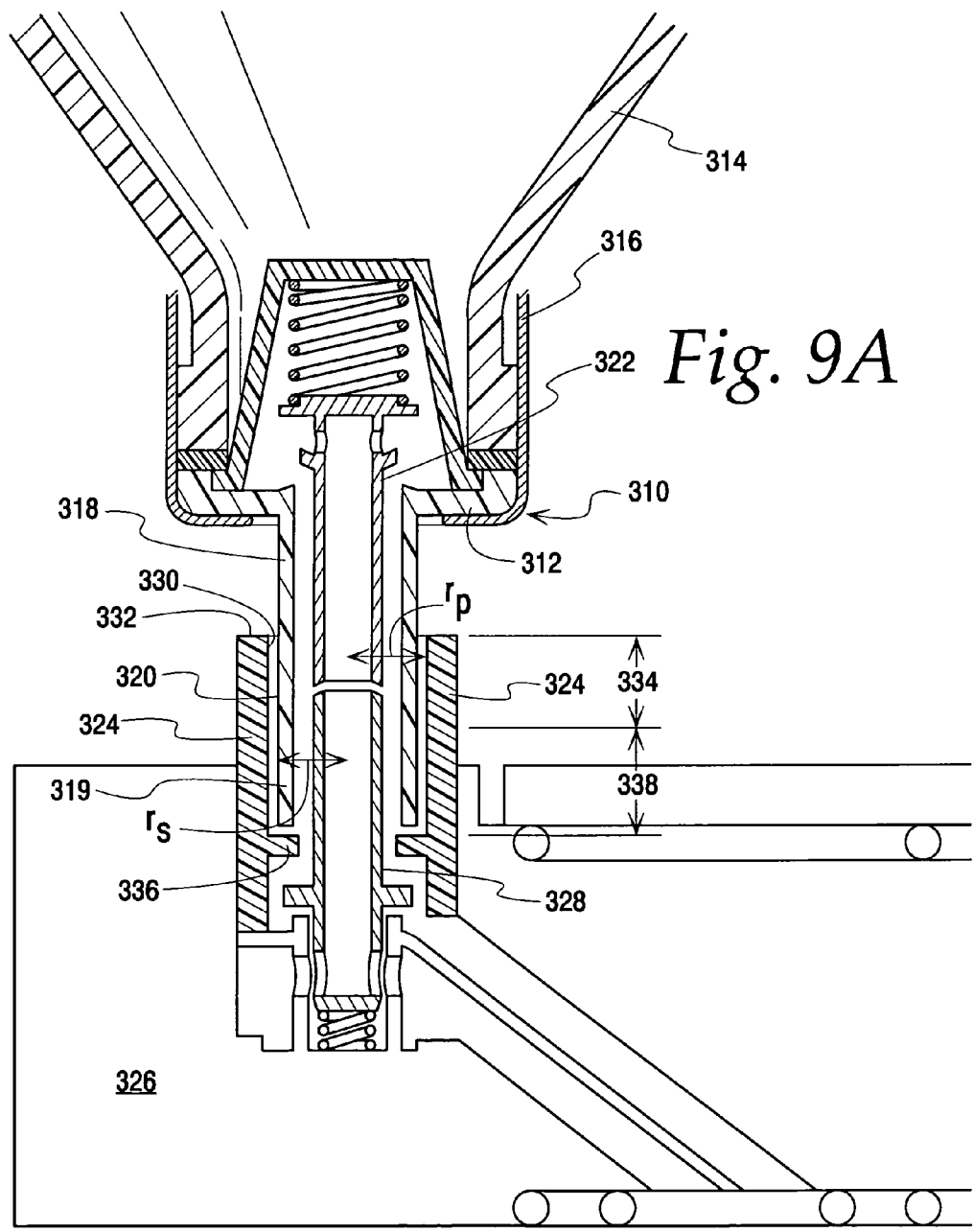
FIG. 9A is a cross-sectional view of an adapter with a spout upper end having a substantially continuous outer radius received in part by a fluid port of an anesthetic vaporizer.

FIG. 9A illustrates another example of an adapter embodying another aspect of the present invention. The adapter 310 includes a base 312 mountable on a container 314 housing an amount of anesthetic agent. The base may be mounted to the container 314 by any suitable means, such as the ferrule 316 illustrated in FIG. 9A. Extending away from the base 312 is a generally tubular spout 318 having an upper end 319 with an outer surface 320 with a substantially continuous outer radius. When used herein in connection with this aspect of the present invention, the term "upper end" refers to the portion of the spout 318 that is inserted into a vaporizer fluid port 324 during fluid transfer. When used herein, the term "substantially continuous outer radius" refers to an upper end with an outer surface that is substantially smooth and free of discontinuities. An o-ring associated with the upper end and a channel for receiving an o-ring are two examples of discontinuities. On the other hand, a smoothly tapered upper end, illustrated in FIG. 9B, has a substantially continuous outer radius and may be preferred over the uniform radius of FIG. 9A in some situations. It will be appreciated that the spout may be provided with a projection according to the above-described prior art keyhole retention system, because such a projection is spaced from the upper end 319.

Fluid flow through the spout 318 is controlled by an adapter valve assembly 322 according to known structure and operation. The upper end 319 of the spout 318 is configured to be received by a fluid port 324 of an anesthetic vaporizer 326. The upper end 319 of the spout 318 is inserted into the fluid port 324 until the adapter valve assembly 322 and a vaporizer valve assembly 328 are opened to allow fluid transfer. Of course, if the vaporizer includes a stop cock, not illustrated, then it must also be opened to allow fluid transfer between the vaporizer 326 and the container 314.

In the embodiment illustrated in FIG. 9A, fluid is transferred from the container 314 to the vaporizer 326 in the absence of a contact seal between the outer surface 320 of the upper end of the spout 318 and an inner surface 330 of the fluid port 324. The outer surface 320 of the upper end 319 of the spout 318 and the inner surface 330 of the fluid port 324 are dimensioned such that a narrow gap exists therebetween. The gap is sufficiently narrow such that leakage of the fluid being transferred to the vaporizer 326 is insubstantial or substantially entirely absent, while still allowing for easy and/or substantially uninhibited removal of the container from the vaporizer. Such a gap is defined by a difference between the inner radius $r_p$ of the fluid port 324 and the outer radius $r_s$ of the spout upper end 319. In one embodiment, the fluid to be transferred from the container 314 to the vaporizer 326 is liquid desflurane, in which case a gap no greater than 0.01 inch is typically adequately sized to prevent leakage of the liquid anesthetic. More preferably, the gap is in the range of approximately 0.001 inch and approximately 0.005 inch. The "shroud" adapter of FIGS. 1 and 2 may be used in combination with the substantially continuous outer radius adapter of FIG. 9A to create an auxiliary sealing arrangement, if desired.

Figure 9B:
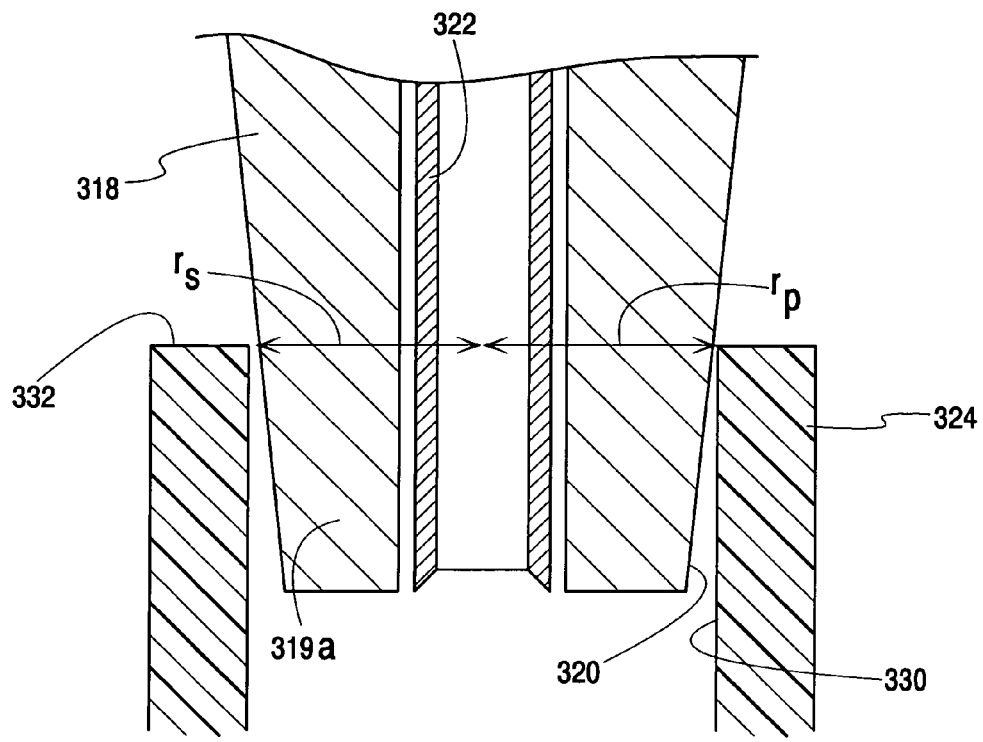
FIG. 9B is a cross-sectional view of an adapter with a tapered spout upper end having a substantially continuous outer radius.

As previously described with reference to the embodiment of FIG. 9A, a spout upper end 319a with a smoothly tapered outer radius $r_s$ may be provided. Such a spout upper end 319a is illustrated in FIG. 9B. If such a tapered spout upper end 319a is defined, then the gap between the outer surface 320 and the fluid port 324 is defined as the minimum gap, which is typically adjacent to an upper lip 332 of the fluid port 324. It will be appreciated by those of ordinary skill in the art that the effectiveness of the fluid seal is dependent on the minimum gap between the spout upper end and the fluid port, so the larger gap surrounding the narrower regions of the spout upper end 319a is contemplated by this aspect of the present invention.

Of course, the relevant outer radius $r_s$ of the spout upper ends illustrated in FIGS. 9A and 9B may be substantially identical to the inner radius $r_p$ of the fluid port 324, such that the gap is eliminated and a press fit is defined, while still allowing for easy removal of the container from the vaporizer. It will be appreciated that such a configuration may result in a press fit between substantially the entire outer surface 320 of the upper end 319 and the fluid port 324 for the substantially uniform outer radius of FIG. 9A. Similarly, if the illustrated outer radius $r_s$ of FIG. 9B is substantially identical to the fluid port inner radius $r_p$, then a press fit may be provided between the spout upper end 319a and the fluid port 324 at a region 334 adjacent to the upper lip 332 of the fluid port 324. This region 334 is referred to herein as an "upper portion" of the fluid port 324 and generally corresponds to the outermost half of the fluid port 324, measured from the upper lip 332 to a vaporizer valve seat 336 that closes the bottom of the fluid port 324. The innermost half 338 of the fluid port 324 is referred to herein as the "lower portion." Of course, the spout upper end will typically form a press fit with the lower portion 338 when the outer radius $r_s$ of the spout 318 is substantially uniform.

The same function may be achieved by provided a spout upper end with an outer radius $r_s$ slightly greater than the inner radius $r_p$ of the fluid port. Of course, in such a configuration, one of the spout upper end and the fluid port is preferably comprised of a material allowing for sufficient "give" or deformation to allow the spout upper end to be inserted into the fluid port. Preferably, the dimensions and/or materials of the adapter spout and the fluid port are selected in order to provide a suitable press fit without undue difficulty in inserting or removing the adapter spout.

Figure 10:
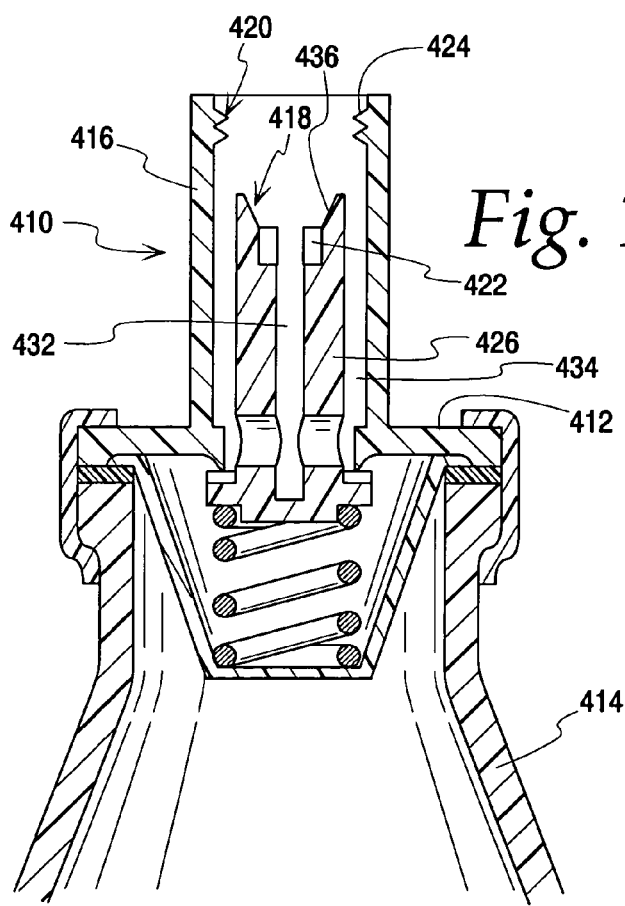
FIG. 10 is a cross-sectional view of an adapter with a retainer mounted on an anesthetic agent container.

FIG. 10 shows an adapter 410 that includes a base 412 mountable on an anesthetic agent container 414 housing an amount of an anesthetic agent. A generally tubular spout 416 extends away from the base 412 and has an associated adapter valve assembly 418 that controls fluid flow through the spout 416. Retainers 420 and 422 are located within the spout 416, associated with the spout 416 and with the adapter valve assembly 418, respectively. As will be seen from the following description, the retainers 420 and 422 perform substantially the same function, so the adapter 410 may be provided with either one of the retainers 420 and 422 or with both, as illustrated in FIG. 10.

Figure 11A:
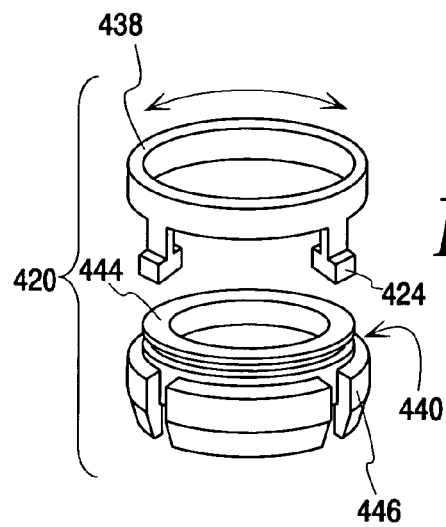
FIG. 11A is a front perspective view of a retainer assembly suitable for use in an adapter.
Figure 11B:
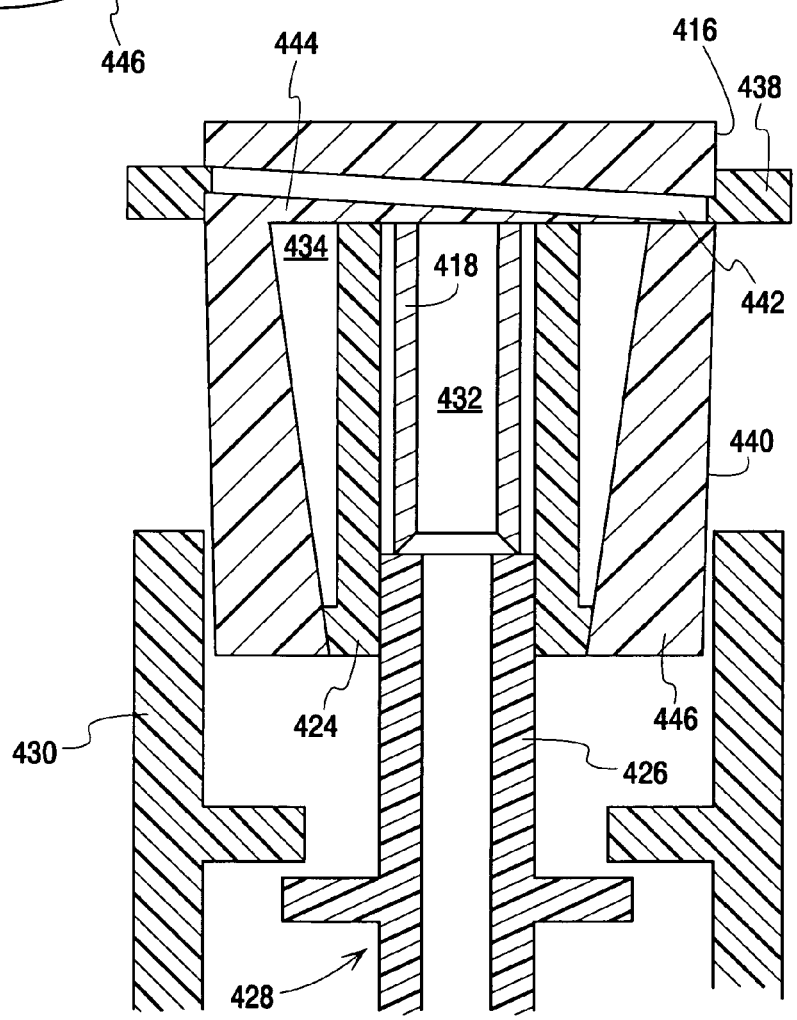
FIG. 11B is a cross-sectional view of the retainer assembly of FIG. 11A, received in part by a fluid port of an anesthetic vaporizer.
Figure 11C:
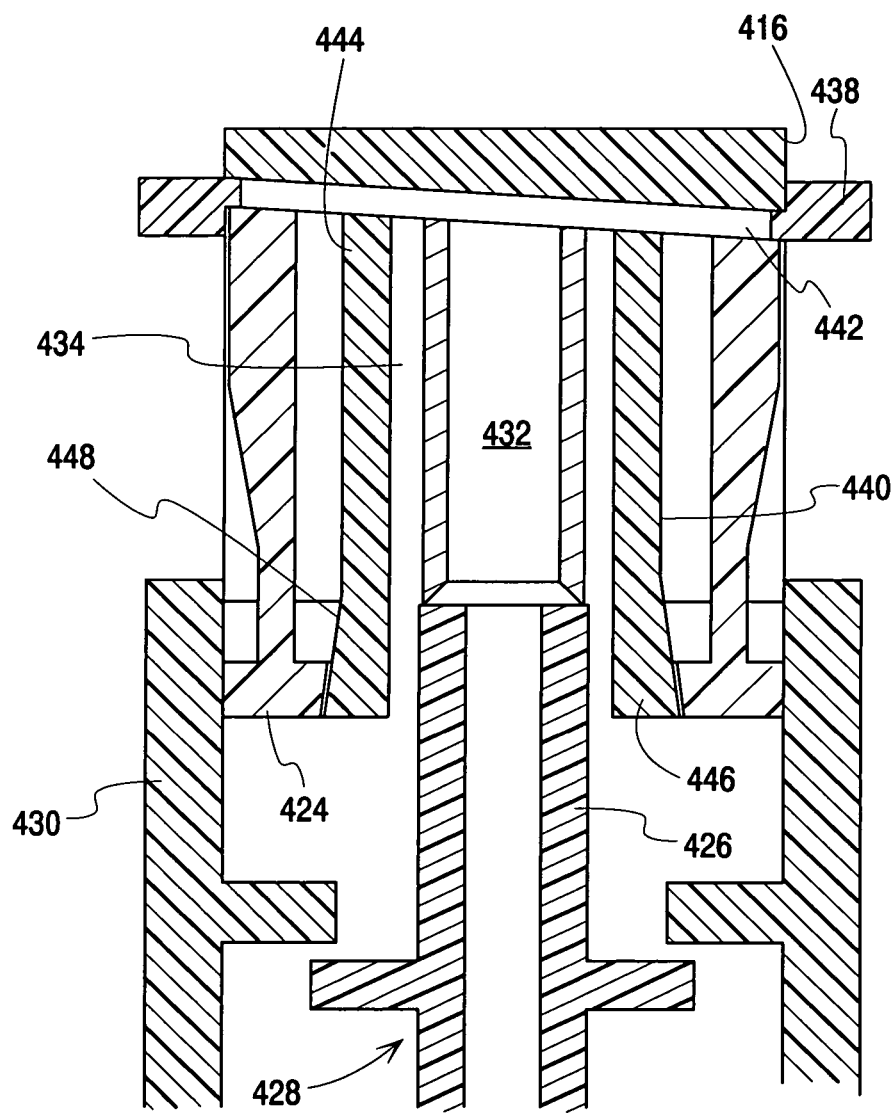
FIG. 11C is a cross-sectional view of an alternative embodiment of the retainer assembly of FIG. 11A.

The retainer 420 associated with the spout 416 is illustrated with inwardly projecting gripping elements, which are illustrated in FIG. 10 as molded teeth 424. The teeth 424 are adapted for locking engagement with a central pin 426 of a vaporizer valve assembly 428 in a vaporizer fluid port 430, as shown in FIG. 11B. In a preferred embodiment of the adapter 410, the adapter valve assembly 418 contacts the central pin 426 to define first and second fluid flowpaths 432 and 434. Typically, a pressurized vapor will flow to the container 414 from the fluid port 430 through the second fluid flowpath 434, so the retainer 420 must lockingly engage the central pin 426 without preventing such flow. Accordingly, the retainer 420 may be defined by discrete elements or at least include open sections for facilitating flow. FIGS. 11A and 11B, which will be described in greater detail herein, show a retainer assembly 420 having teeth 424 suitable for locking engagement with the central pin 426 without preventing fluid flow. Of course, if the fluid transfer is accomplished entirely within the first fluid flowpath 432, then the retainer 420 may form a fluid seal with the central pin 426 without degrading the performance of the adapter 410.

Figure 12:
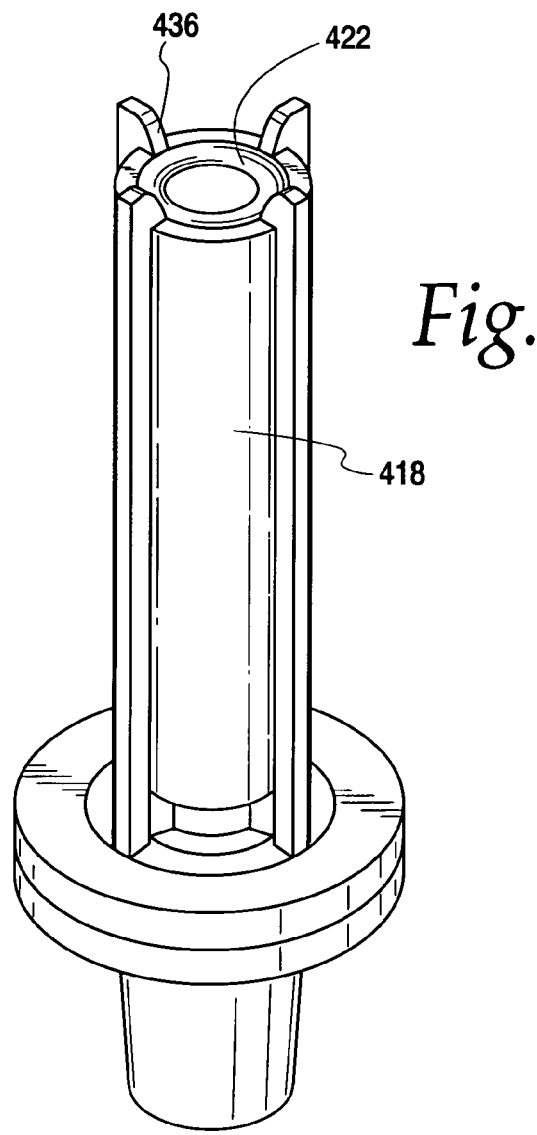
FIG. 12 is a front perspective view of an adapter valve assembly suitable for use in an adapter.

The retainer 422 associated with the adapter valve assembly 418 is also adapted for locking engagement with the central pin 426 to prevent disengagement. As described above, the adapter valve assembly 418 contacts the central pin 426 to define first and second fluid flowpaths 432 and 434. The flowpaths 432 and 434 are separated by contact between the adapter valve assembly 418 and the central pin 426, so it may be preferred for the retainer 422 to form a seal with the central pin 426 when it is engaged thereto. As such, the retainer 422 preferably takes the form of a gasket or elastomeric o-ring adapted for locking- and sealing-engagement with an outer surface of the central pin 426. In a preferred embodiment, illustrated in FIG. 12, the adapter valve assembly 418 includes tapered or angled sections 436 adjacent to the retainer 422 for guiding the central pin 426 to the retainer 422. The central pin 426 is slightly larger than the angled sections 436 and retainer 422, so persistent advancement of the adapter valve assembly 418 against the central pin 426 will effectively wedge the central pin 426 into the retainer 422, thereby creating a sealing and retaining relationship therebetween. The retainer 422 is disengaged from the central pin 426 by persistent removal of the adapter 410 from the fluid port 430.

In use, the spout 416 is inserted into the fluid port 428 until at least a portion of the central pin 426 is received by the retainer 420 and/or 422, as shown in FIG. 11B. When the central pin 426 has been received by the retainer 420 and/or 422, the retainer 420 and/or 422 is moved into locking engagement with the central pin 426. In such a locking condition, the adapter 410 may not be removed from the fluid port 428 until the retainer 420 and/or 422 is disengaged from the central pin 426. Hence, it will be seen that an adapter of the type described above serves as an advantageous alternative to the projection-slot retention arrangement of prior art devices.

Figures 13A, 13B:
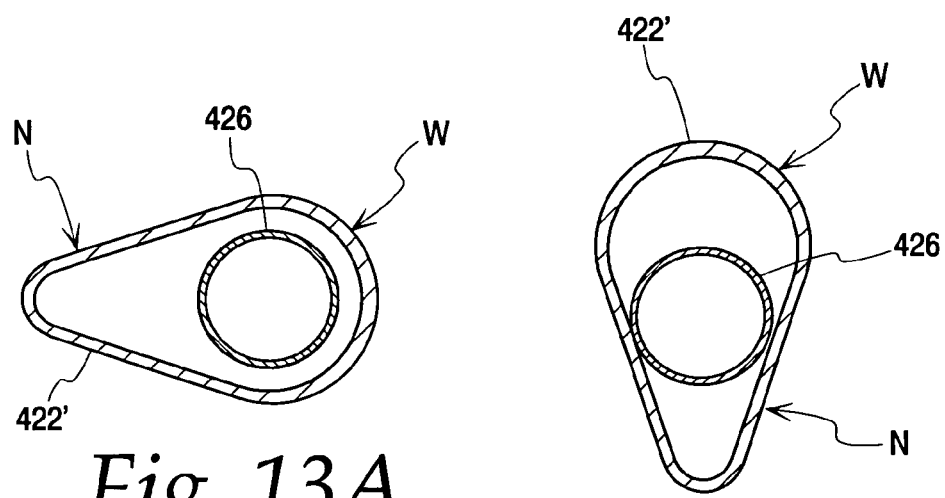
FIG. 13A is a schematic view of a cammed retainer suitable for use in an adapter.
FIG. 13B is a schematic view of the cammed retainer of FIG. 13A, rotated to a different orientation.

Locking the retainer 420 and/or 422 onto the central pin 426 may be achieved in any one of a number of ways, depending on the structure. As described above, the retainer 422 may be actuated by axial movement of the adapter 410. As another example, illustrated schematically in FIGS. 13A and 13B, the retainer 422' may be non-circular or cammed, such that the central pin 426 moves easily through a relatively wide region, generally designated at W, and is locked and retained by a narrower region, generally designated at N. In use, the adapter 410 is inserted into the fluid port 430 with the central pin 426 passing through the relatively wide region W of the retainer 422', as shown in FIG. 13A. Thereafter, the adapter 410 is rotated to the orientation of FIG. 13B, which rotates the cammed retainer 422' and moves the narrower region N into contact with the central pin 426. The central pin 426 becomes wedged in the narrower region N to create a retention relationship during fluid transfer. In order to remove the adapter 410 from the fluid port 430, it must first be rotated to the orientation of FIG. 13A, so that the central pin 426 is released and may again pass through the relatively wide region W of the cammed retainer 422'.

With regard to actuation of a retainer 420 associated with the spout 416, if the retainer is a molded element, such as the teeth 424 of FIG. 10, then locking engagement can be initiated by radially moving the retainer into contact with the central pin 426. Referring now more particularly to FIGS. 11A and 11B, a retainer assembly 420 is illustrated which is comprised of two elements. The first element is a rotatable ring 438 and the second is an inner portion 440. The inner portion 440 is preferably associated with an upper end of the spout 416, while the rotatable ring 438 is rotatable with respect to the inner portion 440. Preferably, the rotatable ring 438 is associated with the inner portion 440 by mating threads 442, such that rotation of the ring 438 will advance it axially with respect to the inner portion 440. Most preferably, an acme screw relationship allows for enhanced axial movement with limited rotation. As best illustrated in FIG. 11B, the inner portion 440 is comprised of a rim 444 and an inwardly tapered skirt 446. The teeth 424 of the rotatable ring 438 are located inwardly of the skirt 446 and arranged such that downward movement of the teeth 424, with respect to the orientation of FIG. 11B, will cause them to contact the skirt 446 and be moved inward.

In use, the spout 416 is inserted into a vaporizer fluid port 430 until at least a portion of the skirt 446 surrounds the central pin 426. The ring 438 remains outside of the fluid port 430, so it may be rotated to axially advance the teeth 424. The teeth 424 contact the tapered skirt 446 and are moved inwardly until they engage and lock onto the central pin 426. In order to provide an improved locking relationship, the teeth 424 may be substantially comprised of an elastomeric material or have an elastomeric coating for contacting the central pin 426. Also, a latching mechanism may be provided to prevent axial movement of the teeth 424 and disengagement of the teeth 424 from the central pin 426. After fluid transfer, the teeth 424 may be removed from the central pin 426 by rotating the ring 438 in the opposite direction to raise and separate the teeth 424. Of course, if a latching mechanism is provided, then it must be disengaged before the teeth 424 can be removed from the central pin 426.

Those of ordinary skill in the art will appreciate that the retainer assembly 420 of FIGS. 11A-11B may be modified to cause the teeth 424 to engage and retain the fluid port 430 instead of, or in addition to, the central pin 426. In particular, the skirt 446 may be provided with an external taper 448, as shown in FIG. 1C, facing the fluid port 430. The teeth 424 would be axially movable along the tapered outer surface of the skirt 446 to separate and engage the fluid port 430. This embodiment may be preferred in some instances, because the teeth 424 may simultaneous provide a retaining function and a sealing function against the fluid port 430, whereas a sealing engagement must typically be avoided if the teeth 424 engage the central pin 426 for the aforementioned reason.

On the other hand, if the retainer is a deformable and/or elastomeric material, then locking engagement can be initiated by radially expanding the retainer until it contacts the central pin 426 or the fluid port 430. Suitable means for causing such deformation include rotation, levering action, axial movement, or the like. It will be appreciated that several embodiments including this aspect provide a retaining arrangement, but not a sealing arrangement between the spout 416 and the fluid port 430, so either conventional sealing means or the inventive sealing arrangements described herein may be used in combination with this aspect of the present invention.

Figure 14A:
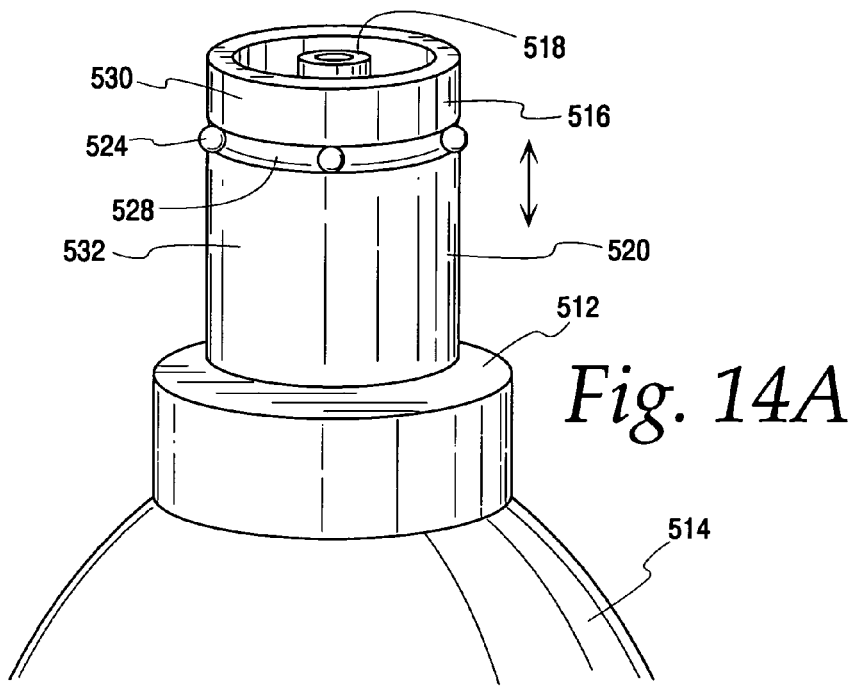
FIG. 14A is a front perspective view of an adapter with a non-continuous sealing member mounted on an anesthetic agent container.
Figure 14B:
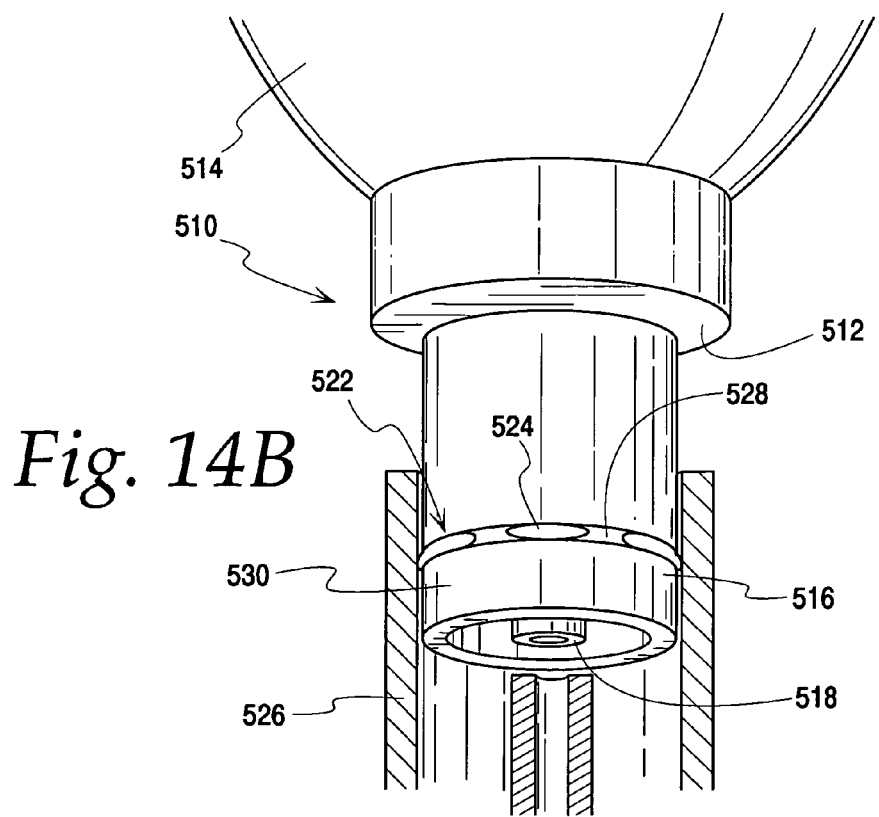
FIG. 14B is a front perspective view of the adapter of FIG. 14A received in part by a fluid port of an anesthetic vaporizer, with the non-continuous sealing member in sealing engagement with the fluid port.

FIGS. 14A and 14B illustrate an adapter 510 that includes a base 512 mountable on an anesthetic agent container 514 housing an amount of an anesthetic agent. A generally tubular spout 516 extends away from the base 512 and has an associated adapter valve assembly 518 that controls-fluid flow through the spout 516. An outer surface 520 of the spout 516 includes a non-continuous sealing member 522 or a plurality of separated members. The non-continuous sealing member 522 generally encircles the spout 516, but may be defined by angularly separated, discrete elements 524. Preferably, the discrete elements 524 are substantially comprised of a deformable and/or elastomeric material.

The spout 516 is adapted to be received by a vaporizer fluid port 526. Fluid flow between the adapter 510 and the fluid port 526 is accomplished in accordance with the above descriptions. In order to provide a fluid seal between the spout 516 and fluid port 526, the non-continuous sealing member 522 is radially expanded or radially moved into contact with the fluid port 526, as illustrated in FIG. 14B. Preferably, each discrete element 524 expands laterally as well in order to close or eliminate the gap between itself and the adjacent discrete elements 524. As the size of the gap between the discrete elements 524 decreases, a more complete fluid seal is formed, so an improved seal may be achieved by selecting a material with enhanced lateral expansion properties or by placing the discrete elements 524 closer together.

FIGS. 14A and 14B illustrate one configuration for radially expanding the non-continuous sealing member(s) 522. In the illustrated embodiment, the non-continuous sealing member 522 is received in a channel 528 defined by a distal portion 530 and a proximal portion 532 of the spout 516. The distal and proximal portions 530 and 532 may be fixed or axially movable with respect to each other. If one of the distal and proximal portions 530 and 532 is axially movable with respect to the other, then such movement will axially compress the non-continuous sealing member 522 and cause it to radially expand, as shown in FIG. 14B. Relative movement of the distal and proximal portions 530 and 532 can be achieved by a number of possible mechanisms, including the actuation knob of FIGS. 6-8 and the deformation mechanisms described previously with respect to the embodiments of FIGS. 10-13B. As the same mechanism may be used with both the retainer of FIGS. 10-13B and the sealing member of FIGS. 14A and 14B, it is contemplated that an adapter incorporating both features, which are simultaneously actuated by the same mechanism, may be preferred for some uses. Of course, rather than deforming and radially expanding to form a fluid seal, the non-continuous sealing member 522 may instead create a seal with the fluid port 526 by outward radial movement. In that case, the movement mechanisms described previously with respect to the embodiments of FIGS. 10-13B or the like may be used.

Figure 15A:
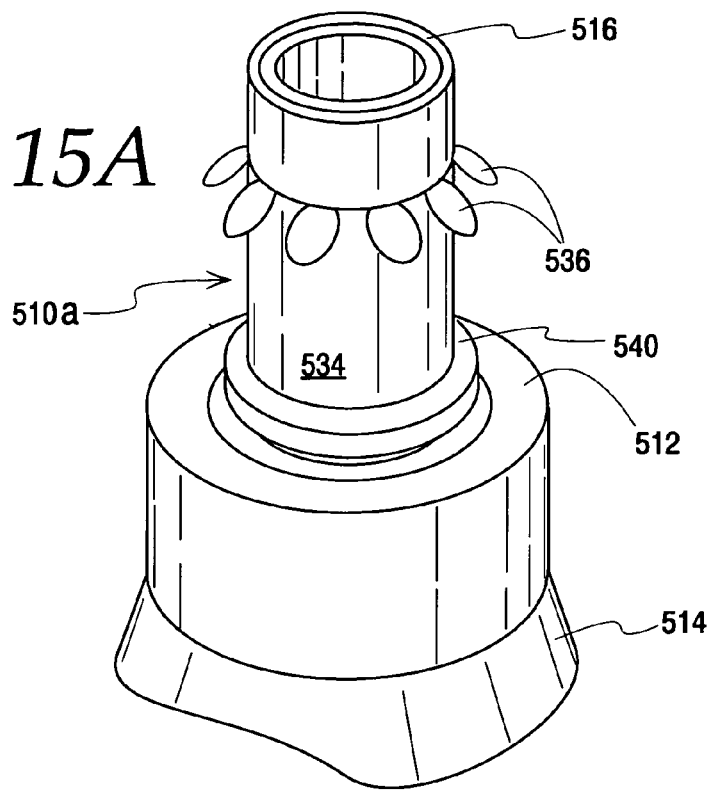
FIG. 15A is a front perspective view of another embodiment of an adapter with a non-continuous sealing member.
Figure 15B:
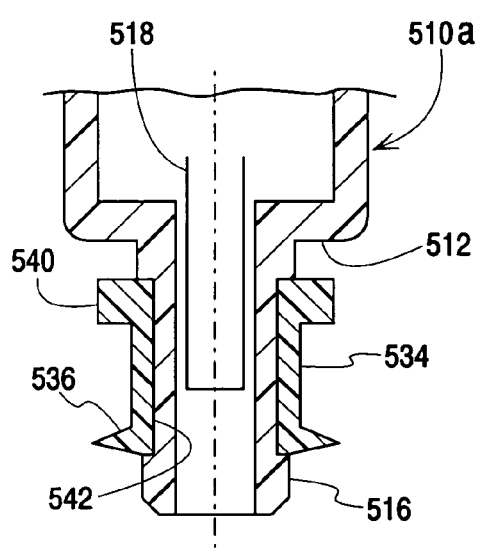
FIG. 15B is a cross-sectional view of the adapter of FIG. 15A.

Other possible embodiments of this aspect are illustrated in FIGS. 15A-17B. For example, FIGS. 15A-15C illustrate an adapter 510a having a spout 516 encircled by an elastomeric overmold 534. The overmold 534 includes a plurality of separate, radially extending petals 536 that are arranged in a ring at a portion of the spout 516 adapted to be received by the fluid port 526 of an anesthetic vaporizer 538 during fluid transfer. In the illustrated embodiment, the elastomeric overmold 534 also includes a locking ring 540 generally adjacent to the base 512 of the adapter 510a. FIG. 15B shows that the spout 516 preferably includes a recess 542 adapted to receive the overmold 534 and to prevent it from moving axially along the spout 516.

Figure 15C:
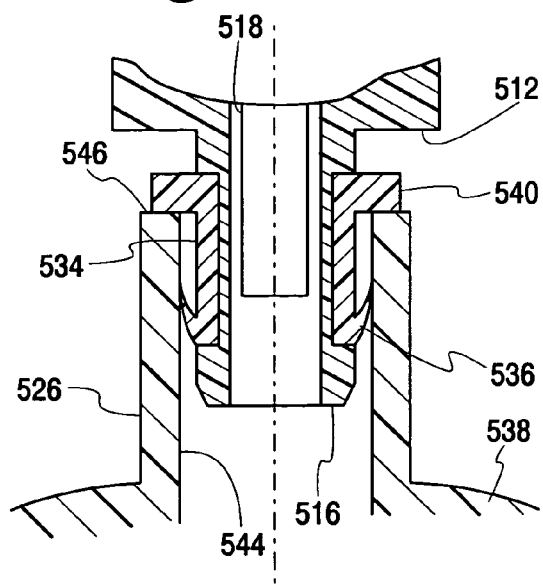
FIG. 15C is a cross-sectional view of the adapter of FIG. 15A, received in part by a fluid port of an anesthetic vaporizer.

The petals 536 are wider than a vaporizer fluid port 526, such that they contact a wall 544 of the fluid port 526 and, as illustrated in FIG. 15C, are folded inwardly toward the spout 516. In the position of FIG. 15C, the petals 534 extend into and substantially occupy the gap between the spout 516 and the wall 544 of the fluid port 526. Thus, it will be appreciated that the petals 536 create a fluid seal during fluid transfer between the adapter 510a and the vaporizer 538. In the illustrated embodiment, the locking ring 540 contacts an upper lip 546 of the fluid port 526 to form an auxiliary fluid seal. It will be understood that the locking ring 540 is an optional aspect of this embodiment of the present invention, as the petals 436 are typically sufficient to create a satisfactory fluid seal. The locking ring 546 may also provide a retaining function instead of, or in addition to, the described sealing function. In particular, the locking ring 546 may serve as an annular projection to be retained by a key-hole slot of an associated anesthetic vaporizer 538, as described previously with respect to prior art devices.

FIGS. 16A and 16B show another embodiment of an adapter 510b having a non-continuous sealing member. The illustrated adapter 510b has a plurality of non-continuous ribs 548 generally adjacent to an outer end of the spout 516. In the illustrated embodiment, the non-continuous ribs 548 are integrally molded with the spout 516. In one embodiment, the individual rib segments 548 may be staggered or offset relative to one another to define one or more tortuous pathways. Of course, it will be appreciated by those of ordinary skill in the art that the ribs 548 need not be integrally molded with the spout 516 and may instead be substantially comprised of an elastomeric material that is affixed to the spout 516 by suitable means.

In use, the spout 516 is inserted into the fluid port 526 of an anesthetic vaporizer. The non-continuous ribs 548 preferably contact a wall 544 of the fluid port 526 in order to substantially occupy the gap between the spout 516 and the fluid port 526. Depending on the size and radial extension of the ribs 548, they may provide a friction-type retention relationship with the fluid port 526. The tortuous pathways defined by the ribs 548 limit and/or substantially prevent the escape of fluid. By doing so, the ribs 548 create a fluid seal during the transfer of anesthetic agent from an anesthetic agent container 514 to the vaporizer.

Figure 17A:
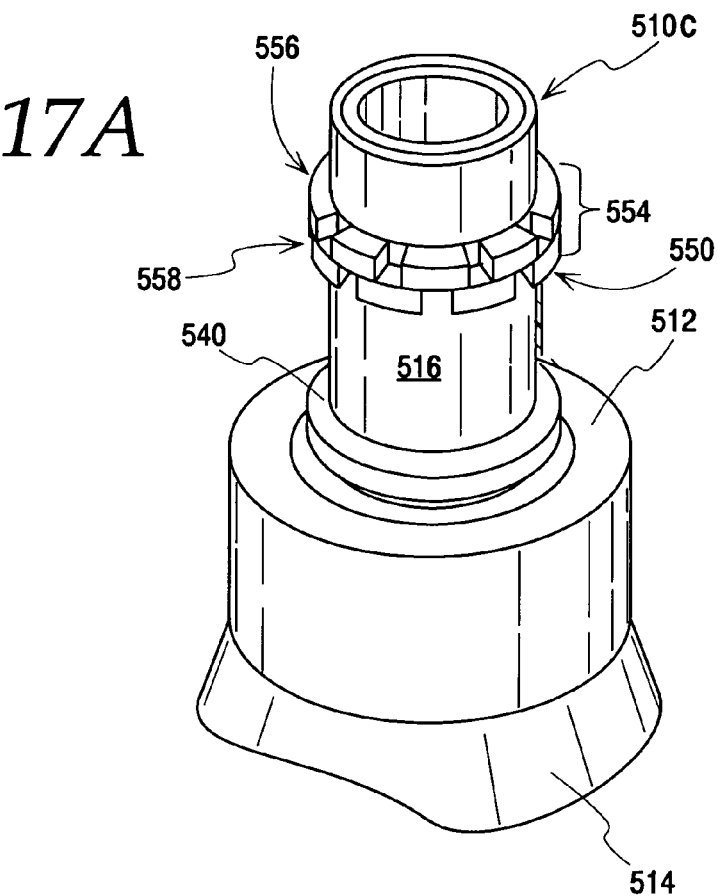
FIG. 17A is a front perspective view of yet another embodiment of an adapter with a non-continuous sealing member.
Figure 17B:
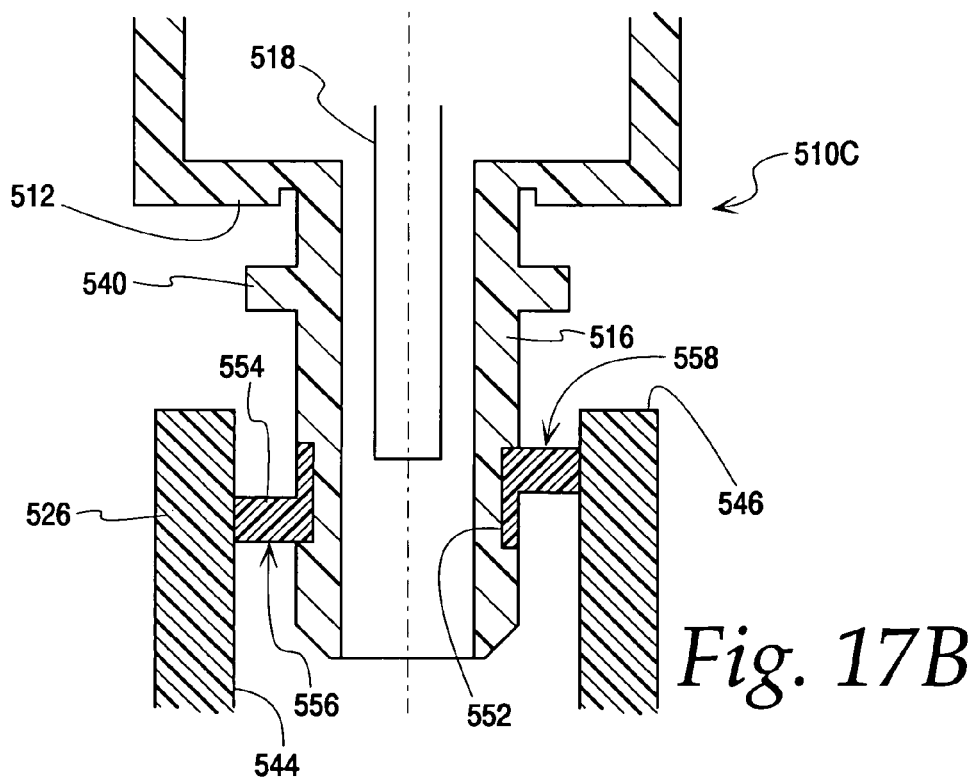
FIG. 17B is a cross-sectional view of the adapter of FIG. 17A, received in part by a fluid port of an anesthetic vaporizer.

FIGS. 17A and 17B show yet another embodiment of an adapter 510c having a non-continuous sealing member. In particular, the adapter 510c has a spout 516 with a discontinuous ring 550 preferably formed of an elastomeric material. As shown in FIG. 17B, the spout 516 preferably includes a recess 552 for receiving the ring 550 and preventing it from moving axially along the spout 516. The spout 516 may also include a locking ring 540, as described above with reference to the embodiment of FIGS. 15A-15C, to provide an auxiliary fluid seal with an upper lip 546 of the fluid port 526 and/or a retention function.

The illustrated ring 550 includes a plurality of radially extending lugs 554 arranged in first and second bands 556 and 558. Possible variations to the illustrated embodiment include the use of a single band or more than two bands and bands that are separate structures associated with the spout 516.

In use, the spout 516 is inserted into the fluid port 526 of an anesthetic vaporizer. The lugs 554 operate similarly to the ribs 548 of FIGS. 16A and 16B, because the lugs 554 of adjacent bands are offset to define tortuous pathways that restrict and/or substantially eliminate the escape of fluid. Preferably, the lugs 554 are slightly wider than the fluid port 526, such that the lugs 554 provide a tight fit against a wall 544 of the fluid port 526. As shown in FIG. 17B, the lugs 554 occupy the gap between the spout 516 and the fluid port 526, resulting in an effective fluid seal during transfer of anesthetic agent to the vaporizer, with a tortuous fluid pathway that limits and/or substantially prevents the escape of fluid. If the spout 516 is provided with a locking ring 540, then the locking ring 540 provides an auxiliary fluid seal and/or a retention function.

Other sealing members, besides those illustrated, are possible and within the scope of the present invention. For example, the spout may be provided with an external screw thread (preferably defining at least one, and more preferably more than one, revolution around the spout) that, with the spout received in the fluid port, may likewise result in a tortuous fluid pathway for limiting fluid escape.

Figure 18A:
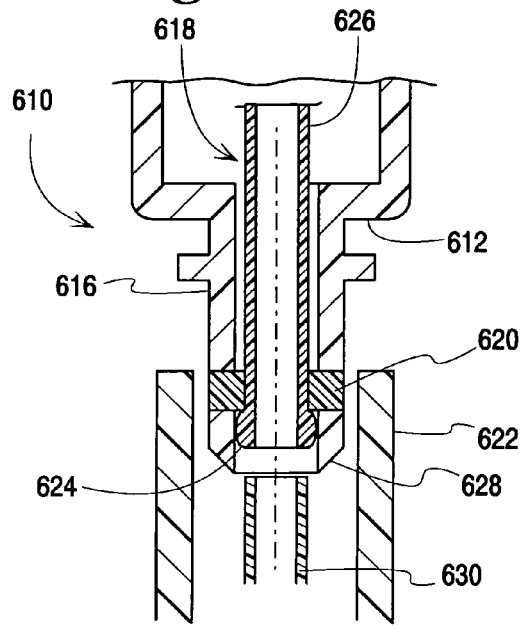
FIG. 18A is a cross-sectional view of an adapter with a spout having a deformable collar portion.
Figure 18B:
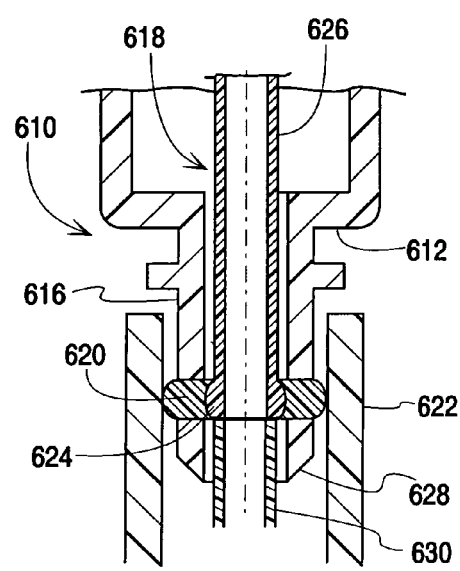
FIG. 18B is a cross-sectional view of the adapter of FIG. 18B received in part by a fluid port of an anesthetic vaporizer, with the deformable collar portion of the spout in an expanded condition.
Figure 18C:
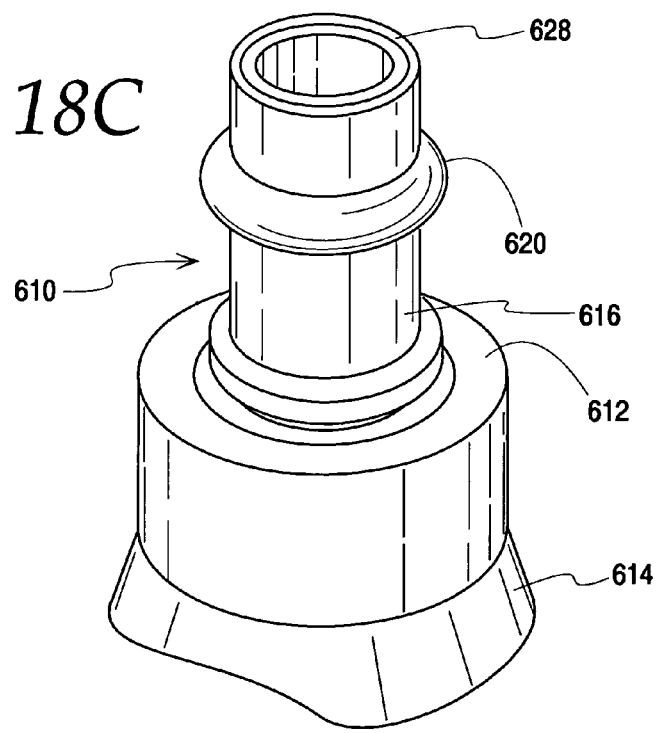
FIG. 18C is a front perspective view of the adapter of FIG. 18A, with the deformable collar portion of the spout in an expanded condition.

FIGS. 18A-18C illustrate an adapter 610 including another embodiment of a sealing system. The adapter 610 includes a base 612 mountable on an anesthetic agent container 614 housing an amount of an anesthetic agent. A generally tubular spout 616 extends away from the base 612 and has an associated adapter valve assembly 618 that controls fluid flow through the spout 616. The spout 616 is defined in part by a deformable collar 620 that communicates with the interior of the spout 616. The deformable collar 620 is comparable in structure to an elastomeric o-ring. The spout 616 is adapted to be received by a fluid port 622 of an anesthetic vaporizer and, as illustrated in FIG. 18A, the outer surface of the collar 620 is configured to also be received by the fluid port 622. Preferably, the outer surface of the collar 620 is substantially plumb with the outer surface of the spout 616 in the unexpanded condition of FIG. 18A.

The adapter valve assembly 618 includes an enlarged head portion 624 that is wider than a body portion 626. In the unexpanded condition of FIG. 18A, the enlarged head portion 624 is disposed between the deformable collar 620 and an open end 628 of the spout 616. Although illustrated at the outermost end of the adapter valve assembly 618, it will be appreciated that the enlarged head portion 624 may be at an intermediate position along the adapter valve assembly 618, provided that it is disposed distally of the deformable collar 620 in the unexpanded condition of FIG. 18A. The enlarged head portion 624 is narrower than the spout 616, such that it may move axially along the interior of the spout 616, but it is wider than an inner surface of the deformable collar 620.

In use, the spout 616 is inserted into the fluid port 622 until the enlarged head portion 624 of the adapter valve assembly 618 contacts a central pin 630 of the anesthetic vaporizer. Contact with the central pin 630 causes the adapter valve assembly 618 to retract into the adapter 610 and open flow through the spout 616, according to conventional design. However, the retraction of the adapter valve assembly 618 brings the enlarged head portion 624 into engagement with the deformable collar 620. The enlarged head portion 624 is more rigid than the deformable collar 620, so it will force the deformable collar 620 radially outwardly until the deformable collar 620 sealingly engages the fluid port 622. This expanded condition may be seen in FIGS. 18B and 18C. In a preferred embodiment, the deformable collar 620 is configured to expand and sealingly engage an upper portion of the fluid port 622. When used in reference to this aspect of the present invention, the term "upper portion" conforms to the above definition in the description of FIGS. 9A and 9B.

In the condition of FIG. 18B, fluid may flow between the adapter valve assembly 618 and the central pin 630. If it is desirable to include separate fluid flowpaths for a liquid anesthetic agent moving into the vaporizer and a pressurized vapor exiting the vaporizer, then the enlarged head portion 624 and/or the deformable collar 620 may be provided with at least one channel, not illustrated, to define a second fluid flowpath through the spout 616.

In order to disengage the deformable collar 620 from the fluid port 622, the adapter 610 is moved away from the fluid port 622. This initial retraction movement of the adapter 610 from the fluid port 622 causes the central pin 630 to separate from the enlarged head portion 624. According to conventional design, the adapter valve assembly 618 is spring-biased to the condition of FIG. 18A, so it will return to that condition as the adapter 610 moves away from the fluid port 622. Movement of the adapter valve assembly 618 to the condition of FIG. 18A disengages the enlarged head portion 624 from the deformable collar 620 which, in turn, returns to the unexpanded condition of FIG. 18A, and allows the adapter 610 to be fully removed from the fluid port 622.

Figure 19A:
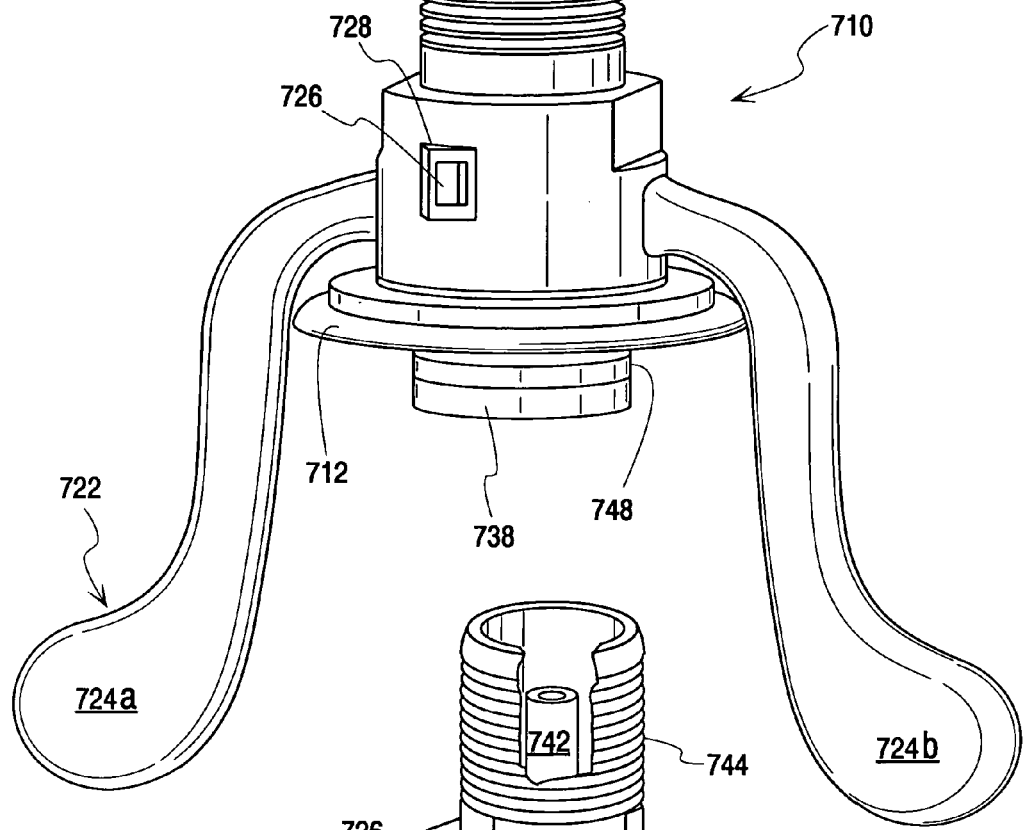
FIG. 19A is a front perspective view of an adapter having a spout that is movable with respect to a base of the adapter to allow fluid flow through the spout.
Figure 19B:
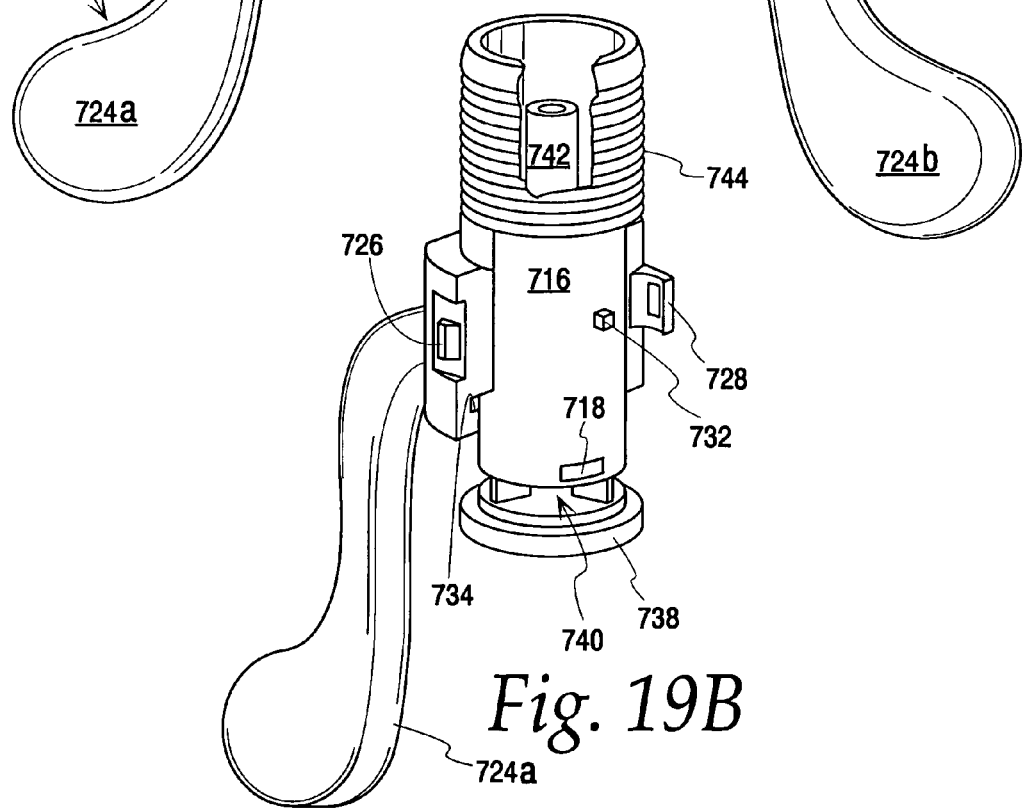
FIG. 19B is a front perspective view of the adapter of FIG. 19A, with selected components removed or broken away for illustrative purposes.
Figure 19C:
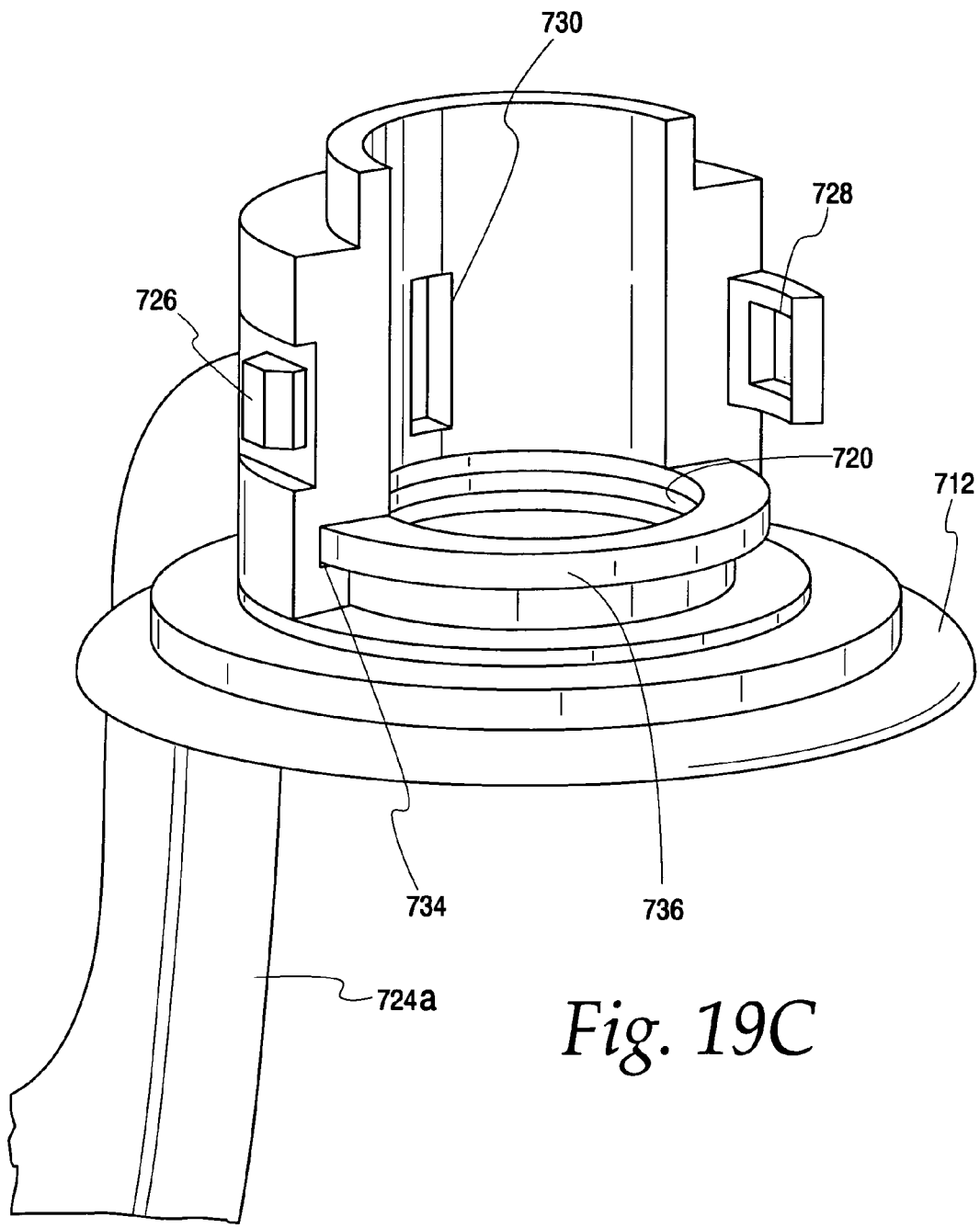
FIG. 19C is a detail view of the base and a handle half of the adapter of FIG. 19A.

FIGS. 19A-19D illustrate an adapter 710 having yet another sealing system. The adapter 710 includes a base 712 mountable on an anesthetic agent container 714 housing an amount of an anesthetic agent. A generally tubular spout 716 extends away from the base 712 and is separate therefrom, such that it may move axially or rotate with respect to the base 712. The illustrated spout 716 is associated with the base 712 by at least one external thread 718, as shown in FIG. 19B, that moves within a mating internal thread 720 of the base 712, which is shown in FIG. 19C. This association can be understood with reference to a typical screw thread, in that the spout 716 is rotated with respect to the base 712 in order to move it axially with respect to the same. As will be clear from the following description, this particular configuration is merely exemplary and other means of axially moving the spout 716 with respect to the base 712 may be practiced without departing from the scope of the present invention.

The illustrated spout 716 also includes a handle 722 comprised of substantially identical first and second halves 724a and 724b. The first and second halves 724a and 724b are joinable together by mating pegs 726 and windows 728 or other suitable means. A slot 730 of the handle 722 receives a post 732 of the spout 716, which allows the handle 722 to move axially along the spout 716, but prevents rotation of the handle 722 with respect to the spout 716. By this system, it will be appreciated that the spout 716 may be rotated by the handle 722.

Each half 724a and 724b of the handle 722 also includes a channel 734 that receives an upper rim 736 of the base 712. This allows the handle 722 to rotate about the base 712 without axial movement. Thus, to summarize the above-described relationships, the handle 722 is rotated about the base 712, which rotates the spout 716 and causes it to move axially with respect to the base 712. The bottom end 738 of the spout 716 includes openings 740 that communicate with a central tube 742 within the interior of the spout 716. The spout 716 is moved axially with respect to the base 712 in order to cover and uncover these openings 740, as will be described in greater detail herein.

The illustrated spout 716 includes a radially expandable member 744 that is comparable in structure and function to the radially expandable member 228 of FIGS. 6-7B. However, instead of using a cammed knob to actuate the radially expandable member, the spout 716 retracts with respect to the handle 722, which compresses the radially expandable member 744 and causes it to outwardly deform to sealingly engage a fluid port 746 in which the spout 716 is received.

Figure 19D:
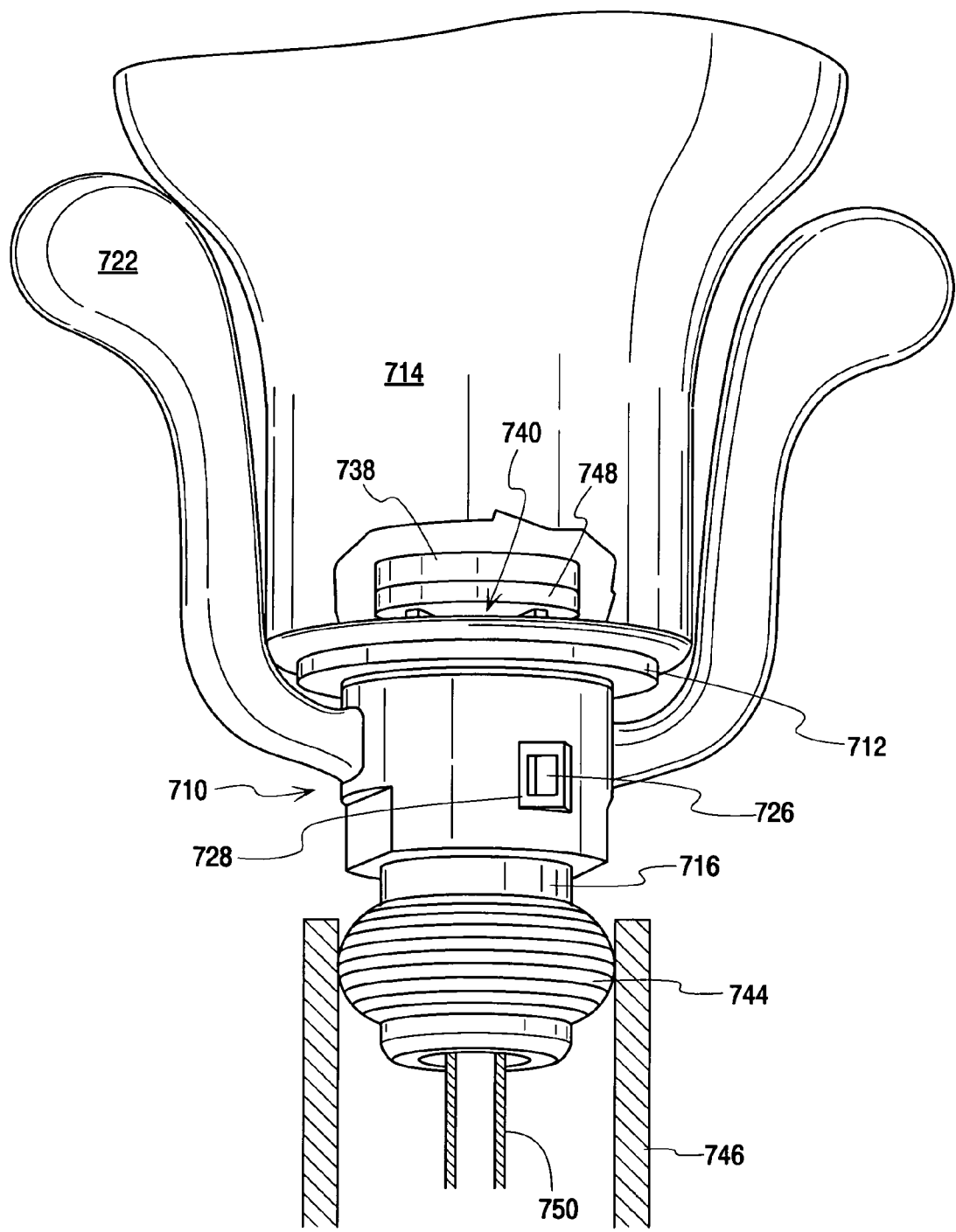
FIG. 19D is a front perspective view of the adapter of FIG. 19A received in part by a fluid port of an anesthetic vaporizer.

In use, the spout 716 is inserted into a fluid port 746 of an anesthetic vaporizer with the openings 740 covered by the base 712. The spout bottom end 738 may be provided with an o-ring 748 to form a fluid seal with the base 712 in order to prevent fluid flow through spout 716. When the spout 716 is sufficiently received by the fluid port 746, typically when the central tube 742 has engaged a central pin 750 of the vaporizer and moved it into an open position, the handle 722 is rotated. As described above, rotation of the handle 722 causes the spout 716 to retract into the base 712, thereby expanding the radially expandable member 744 to sealingly engage the fluid port 746 and exposing the openings 740 to allow flow through the spout 716. This condition is illustrated in FIG. 19D. As an alternative to rotating the handle 722, if an anesthetic container 714 is rigidly affixed to the base 712, then the handle 722 may be held stationary while the container 714 is rotated in order to retract the spout 716.

As best shown in FIG. 19B, the central tube 742 is preferably spaced away from the inner wall of the spout 716 in order to define separate flowpaths through the central tube 742 and through the space between the central tube 742 and the spout 716. This configuration may be preferred for transferring an anesthetic agent such as desflurane to the vaporizer, because provision must be made for the transfer of pressurized vapor from the vaporizer to the container 714.

When the vaporizer has been filled, the handle 722 or container 714 is rotated in the opposite direction to move the spout 716 away from the base 712, which closes the openings 740 and disengages the radially expandable member 744 from the fluid port 746. From the preceding description, it will be clear to those of ordinary skill in the art that rotation is simply one way of allowing flow through the spout 716, so other means of retracting the spout 716 are within the scope of the present invention.

FIG. 20 shows an adapter 810 having a pivoting retainer 812 for securing an anesthetic agent container 814 to an anesthetic vaporizer, a portion of which is generally designated at 816. The adapter 810 illustrated in FIG. 20 may be better understood with further reference to the embodiment of FIGS. 1 and 2. The adapter 810 has a base 818 mountable on an anesthetic vaporizer 816, about a fluid port, which is not visible in FIG. 20. If the fluid port is movable with respect to the vaporizer 816, then the adapter 810 is preferably adapted to be movable with the fluid port. A sidewall 820 extends away from the base 818 to an upper end 822. The upper end 822 includes an opening, not visible in FIG. 20, for receiving a portion of an anesthetic agent container 814, typically a spout thereof.

The pivoting retainer 812 may be pivotally connected to the adapter 810 and extends away therefrom. Preferably, the pivoting retainer 812 is connected to the adapter sidewall 820 so as to prevent interference with an anesthetic agent container 814 that is inserted into the fluid port. In FIG. 20, the pivoting retainer 812 is illustrated as a generally rigid U-shaped bracket or stirrup with first and second legs 824 and 826 that are connected to opposite lateral sides of the adapter sidewall 820. The first and second legs 824 and 826 are connected to each other by a transverse leg 828. If a rigid retainer is provided, then it may be defined by a bent metal wire or as a molded plastic piece. Preferably, the legs of the retainer are shaped to accommodate an anesthetic agent container that is fully inserted into the fluid port, as described below.

As containers of various sizes may be used with the vaporizer, the retainer 812 is preferably removably connected to the adapter 810, such that the user may replace one retainer with another that is better suited for a particular container. Alternatively, the container 814 may be provided with structures comparable to the first and second legs 824 and 826 that are receivable by the sidewall 820 of the adapter 810. According to yet another embodiment, the pivoting retainer 812 may be substantially comprised of a deformable or elastic material. This may be preferred to a rigid or metal bracket, because a single retainer can accommodate a wider variety of container sizes.

Initially, the pivoting retainer 812 is positioned in a generally downward or upward condition, in terms of the orientation of FIG. 20, such that there is a clear path for an anesthetic agent container 814 to be inserted into the vaporizer fluid port. When the container spout has been at least partially inserted into the adapter 810, the pivoting retainer 812 is pivoted into the position of FIG. 20 for engagement with a portion of the container 814. It will be appreciated that the retainer 812 engages the container 814 in order to prevent accidental separation of the adapter 810 and the spout during fluid transfer. The pivoting retainer 812 is illustrated in FIG. 20 as engaging a bottom end 830 of the container 814, but other configurations are possible. For example, the retainer may engage other portions of the container 814, such as a ferrule or projection 832, if provided, in order to prevent accidental removal of the spout from the vaporizer 816.

Figure 21:
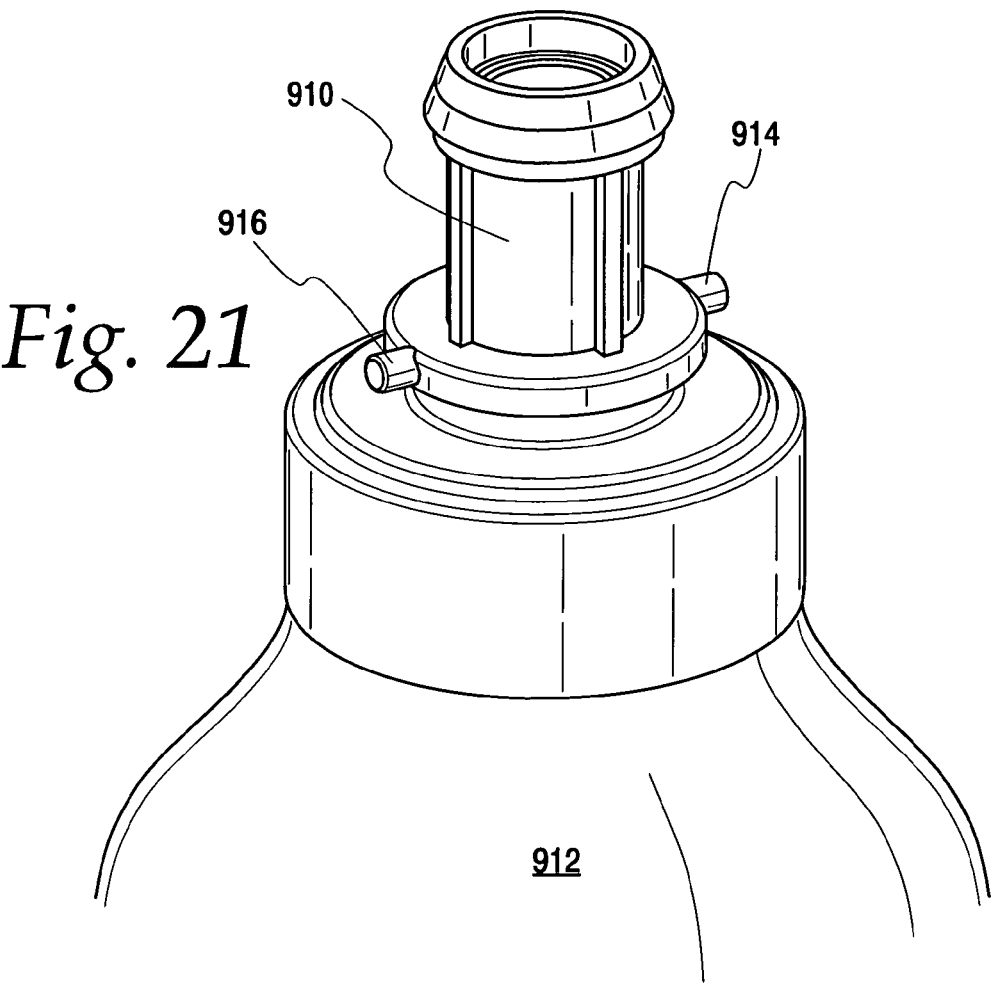
FIG. 21 is a front perspective view of a container spout having a retaining post.
Figure 22:
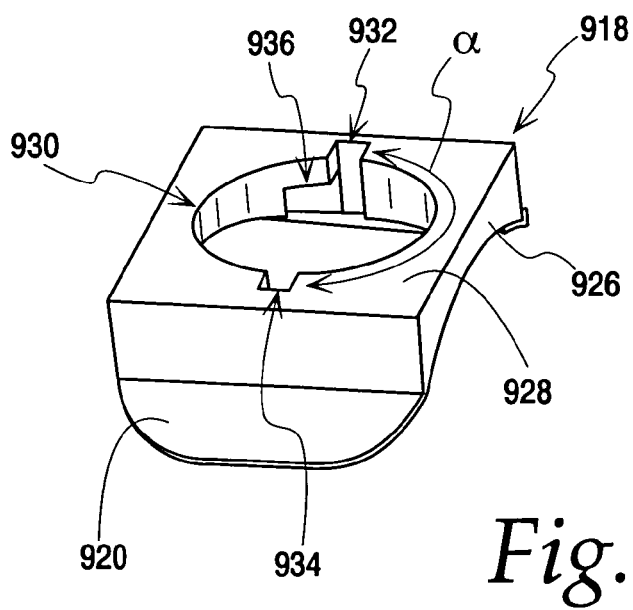
FIG. 22 is a front perspective view of an adapter suitable for receiving and retaining the container spout of FIG. 21.
Figure 23:
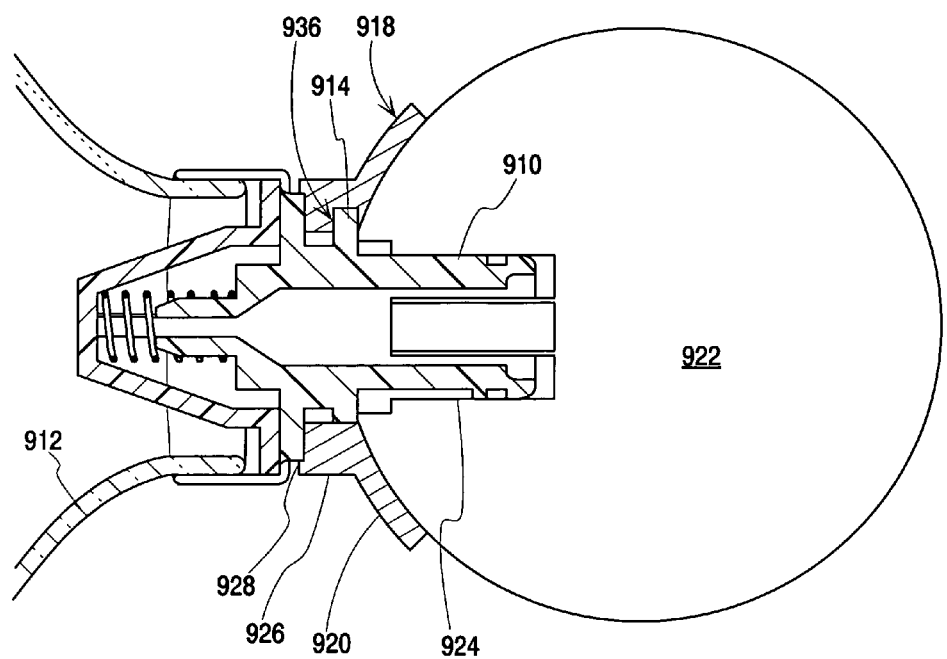
FIG. 23 is a cross-sectional view of the container spout of FIG. 21 in engagement with the adapter of FIG. 22.

Another example of a retention system for establishing fluid communication between an anesthetic agent container and an anesthetic vaporizer is provided in FIGS. 21-23. More particularly, FIG. 21 shows a generally tubular spout 910 associable with an anesthetic agent container 912 and having a plurality of retaining posts 914 and 916 that extend radially away from the spout 910, although it will be appreciated from the following description that only one post may be necessary. The spout 910 is configured to be received by an adapter 918 mountable about an anesthetic vaporizer fluid port, such as, but not limited to, an adapter of the type shown in FIGS. 1 and 2.

As illustrated in FIGS. 22 and 23, the adapter 918 preferably has a base 920 securable to an anesthetic vaporizer 922, surrounding a fluid port 924. If the fluid port 924 is movable with respect to the vaporizer 922, then the adapter 918 is preferably adapted to be movable with the fluid port 924. A sidewall 926 extends away from the base 920 to an upper end 928. The upper end 928 defines an opening or aperture 930 for receiving the spout 910. The aperture 930 includes slots 932 and 934 for receiving the retaining posts 914 and 916, respectively, as the spout 910 is moved into the adapter 918. Each slot includes a lateral pocket 936, only one of which is visible in FIG. 22, which is spaced away from the upper end 928 of the adapter 918.

In use, the posts 914 and 916 are aligned with the slots 932 and 934, respectively, and the spout 910 is advanced into the adapter 918 and the associated fluid port 924. When the spout 910 has been sufficiently advanced into the adapter 918, it is rotated to move the posts into the lateral pockets, illustrated in FIG. 23 for the first post 914 and the first pocket 936. Preferably, rotation of the spout 910 simultaneously moves the first retaining post 914 into the first pocket 936 and the second retaining post 916 into the second pocket, not illustrated. When the posts are moved into the pockets, the spout cannot be removed from the adapter and fluid port without rotating the posts back into alignment with the slots. Hence, it will be appreciated that the posts, the slots, and the pockets provide a bayonet locking or retention system.

According to one embodiment, illustrated generally in FIG. 23, a portion of the spout 910 may contact the upper end 928 to form a fluid seal when the post 914 is received by the pocket 936. In another embodiment, a tighter seal may be achieved by providing an adapter with a downwardly spiraling or angled pocket, not illustrated, such that rotation of the post into the pocket pulls the spout further into the adapter.

The spout and adapter may be provided with any number of mating posts and slots, and different orientations may be provided for different anesthetic agents. In particular, if two slots 932 and 934 are provided, then they may be separated by an indexing angle α, as shown in FIG. 22. The indexing angle depends on the anesthetic agent to be delivered to the vaporizer. For example, an adapter for desflurane may be provided with two diametrically opposed slots, as illustrated in FIG. 22, whereas an enflurane adapter may instead have two slots separated by 90 degrees, such that only a spout having the correct post configuration may be received by the adapter. This provides a retention function, while also preventing the use of an improper anesthetic agent with the vaporizer.

Figure 24A:
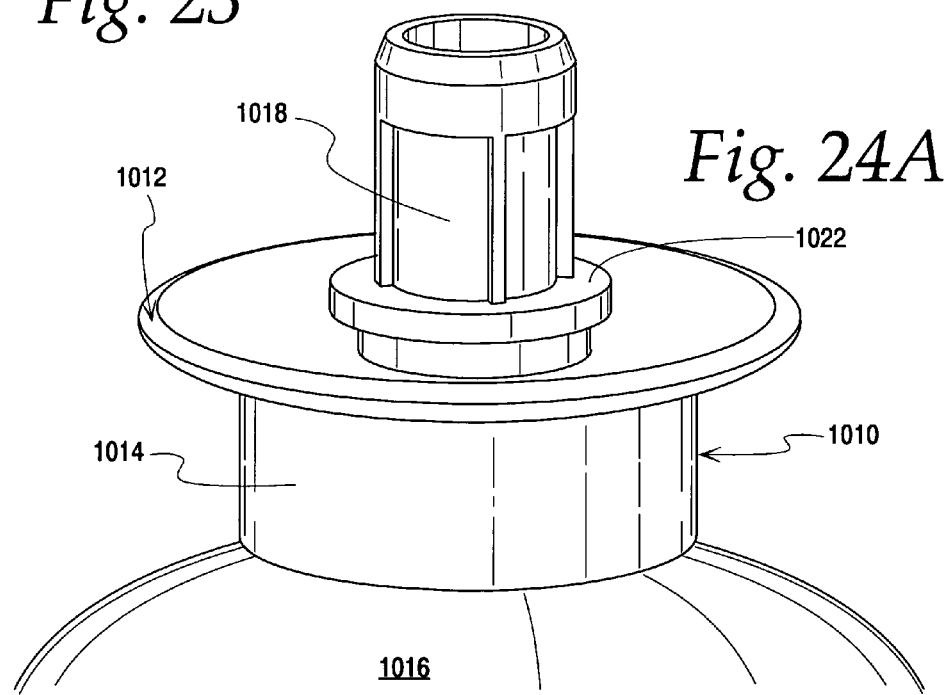
FIG. 24A is a front perspective view of an adapter having a splash guard.
Figure 24B:
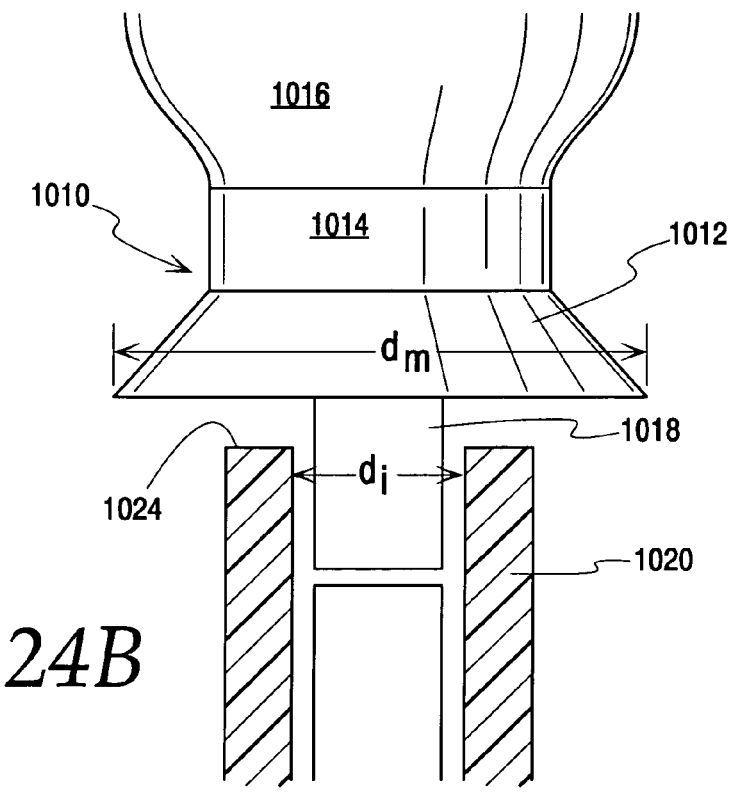
FIG. 24B is a side elevational view of the adapter of FIG. 24A, with selected components removed, received in part by a fluid port of an anesthetic vaporizer.
Figure 25:
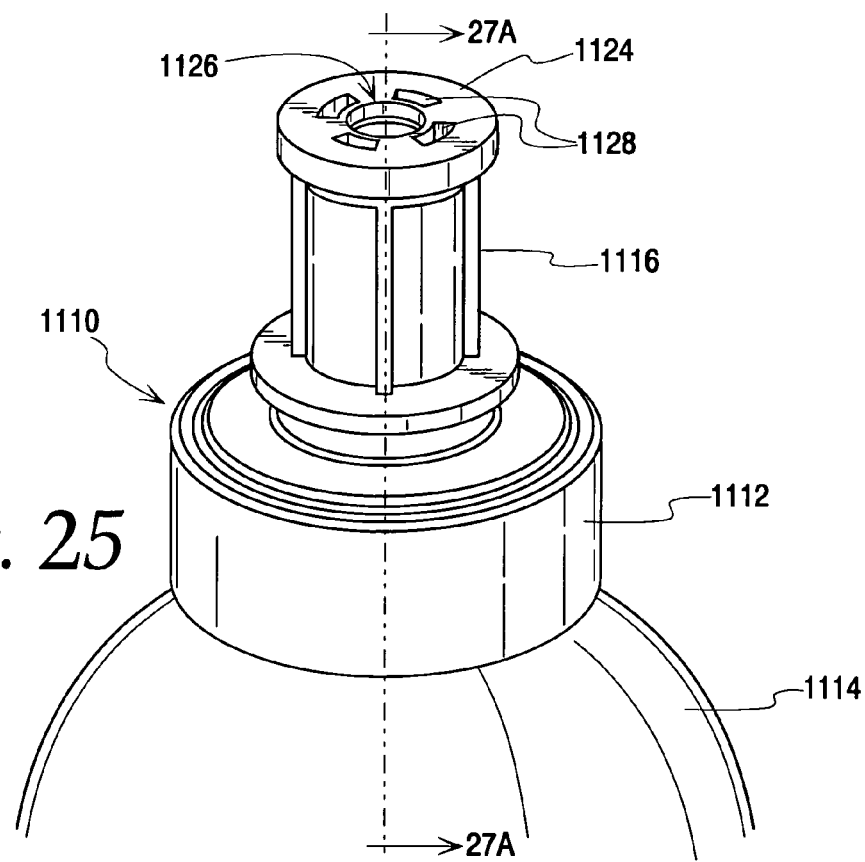
FIG. 25 is a front perspective view of an adapter having a rotatable valve disk.
Figure 26:
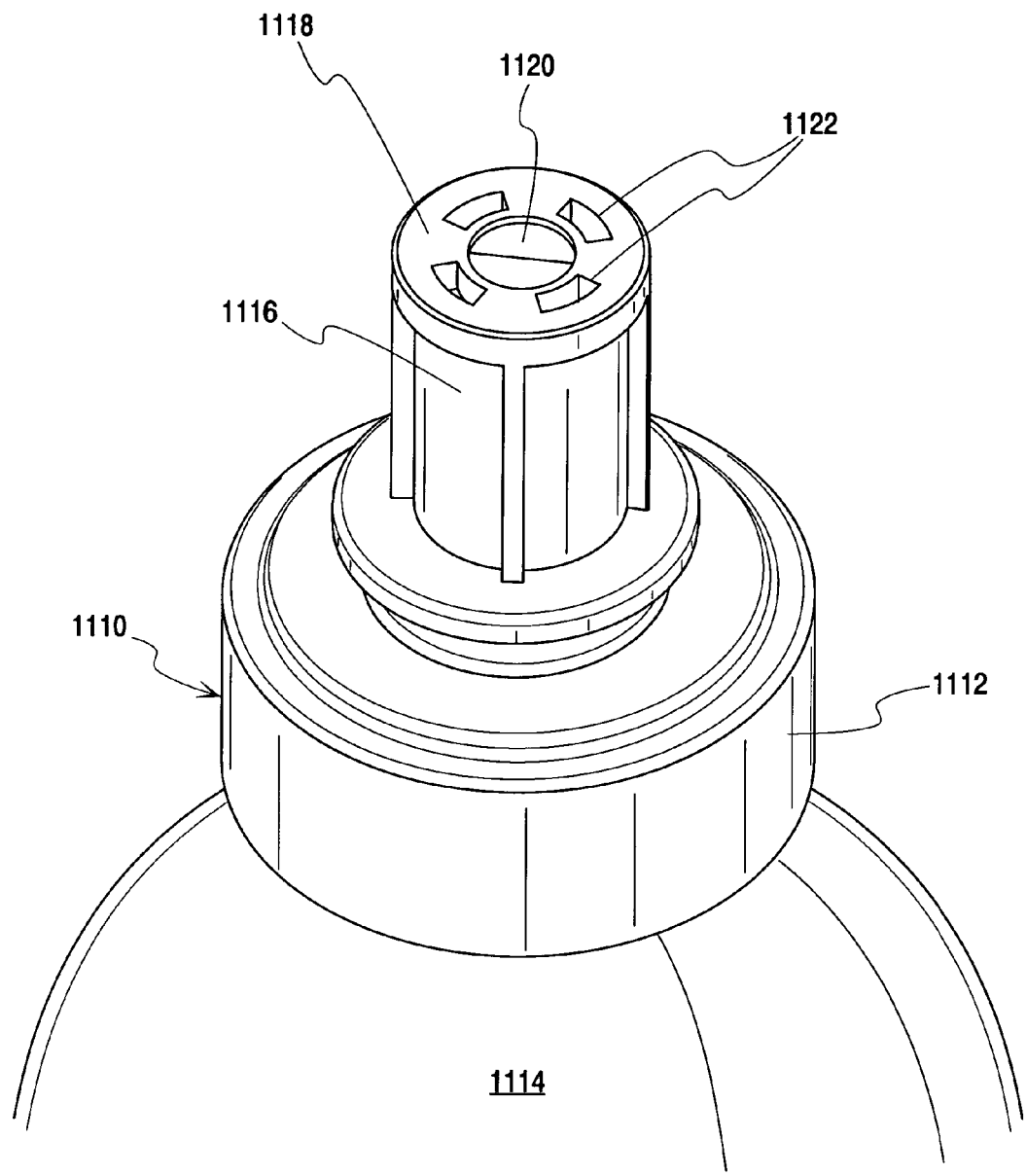
FIG. 26 is an enlarged front perspective view of the adapter of FIG. 25, illustrated without the rotatable valve disk.

FIGS. 24A and 24B illustrate an adapter 1010 having a shielding member or splash guard 1012. As will be described herein, the shielding member 1012 substantially prevents backspray of anesthetic agent from a fluid port of an anesthetic vaporizer when a spout of the adapter is received by the fluid port. In addition to the shielding member 1012, the adapter 1010 further includes a base 1014 associable with an anesthetic agent container 1016 and a generally tubular spout 1018 extending away from the base 1014. The spout 1018 is configured to be received by a fluid port 1020 of an anesthetic vaporizer, as illustrated in FIG. 24B.

The shielding member, which may be a generally annular structure, may be associated with the base of the adapter, the spout, or both. In a preferred embodiment, best shown in FIG. 24B, the shielding member 1012 has a frusto-conical profile extending distally from a minimum diameter to a maximum diameter $d_m$. As shown in FIG. 24A, the adapter spout 1018 may be provided with a locking ring 1022, according to the above discussion of the embodiment of FIGS. 15A-15C. If the adapter spout includes a locking ring suitable for use in a keyhole retention system, then the shielding member is preferably adapted to avoid interference with a curved slot of the vaporizer during fluid transfer.

In use, the spout 1018 is inserted into the fluid port 1020 of an anesthetic vaporizer. With the spout 1018 fully inserted into the fluid port 1020, the shielding member 1012 remains outside of the fluid port 1020 during fluid transfer and is spaced from an upper lip 1024 of the fluid port 1020, as illustrated in FIG. 24B. Preferably, the maximum diameter $d_m$ of the shielding member 1012 is larger than the inner diameter $d_i$ of the fluid port upper lip 1024, such that liquid or vapor escaping from the fluid port 1020 during fluid transfer is intercepted and deflected by the shielding member 1012 before it can come into contact with an operator. It will be appreciated by those of ordinary skill in the art that this aspect of the present invention may be used alone or in combination with a number of the other embodiments described herein.

The amount of blowback or backspray from the fluid port depends on a number of factors, such as the integrity of the fluid seal between the container spout and the fluid port, the type of anesthetic being transferred, the nature of the anesthetic vaporizer, etc. In a preferred embodiment, which is believed to be well-suited for use with a typical desflurane container spout and desflurane vaporizer, the maximum diameter $d_m$ of the splash guard is at least approximately 50% greater than the inner diameter $d_i$ of the fluid port upper lip. Such a splash guard will prevent desflurane blown out of the fluid port from contacting the operator. More preferably, for the same procedure, the maximum diameter $d_m$ of the splash guard is in the range of between approximately 75% and approximately 125% greater than the inner diameter $d_i$ of the fluid port upper lip.

FIGS. 25-27B illustrate an adapter 1110 with a base 1112 which is mountable on an anesthetic agent container 1114. A generally tubular spout 1116 of the adapter 1110 extends away from the base 1112 to a distal end 1118 which is preferably topped by a sealing membrane 1120, illustrated in FIG. 26 as a split septum. The sealing membrane 1120 is surrounded by at least one through hole 1122 that passes through the distal end 1118. A rotatable valve disk 1124 is associated with the distal end 1118 of the spout 1116 and mounted for rotation with respect to the same. The rotatable valve disk 1124 includes a central opening 1126, which allows access to the sealing membrane 1120, and at least one through hole 1128 that correspond generally to the through holes 1122 of the spout distal end 1118.

Figure 27A:
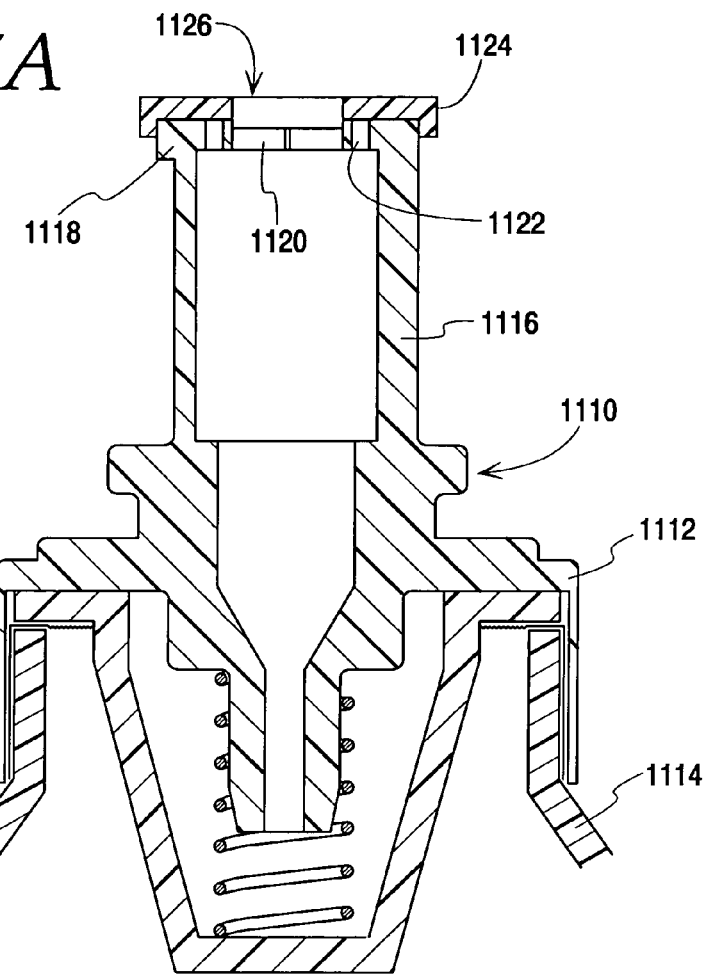
FIG. 27A is a cross-sectional view of the adapter of FIG. 25, taken through the line 27A-27A of FIG. 25, with the rotatable valve disk in an open position.
Figure 27B:
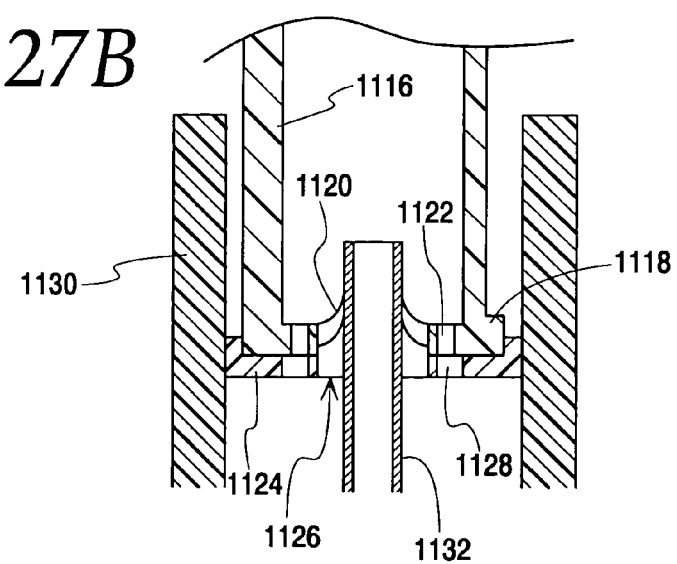
FIG. 27B is a cross-sectional view of the adapter of FIG. 25, received in part by an anesthetic vaporizer fluid port.

In a closed position, illustrated in FIG. 27A, the spout through holes 1122 are misaligned with the disk through holes 1128, such that fluid may not flow out of the anesthetic agent container 1114 associated with the adapter 1110. When the term "misaligned" or any of its variations are used herein with regard to the embodiment of FIGS. 25-27B, it is intended to refer to a situation wherein the spout through holes 1122 are completely covered by the valve disk 1124, such that fluid cannot flow through the spout through holes 1122. However, if a disk through hole 1128 at least partially overlays a spout through hole 1122, then they are aligned and in an open position that allows flow therethrough, as shown in FIG. 27B. Hence, it will be appreciated that this system provides an adapter valve assembly, as the term has been used herein. Thus, it is contemplated that an adapter valve assembly according to this embodiment may be used with other aspects of the present invention in order to regulate flow through a spout.

In use, the adapter spout 1116 is inserted into the fluid port 1130 of an anesthetic vaporizer, not illustrated. A central pin 1132 of the fluid port 1130 is received by the central opening 1126 of the disk 1124 and passes through the sealing membrane 1120 of the spout 1116. The disk 1124 is then rotated to the position of FIG. 27B to bring the disk through holes 1128 into alignment with the spout through holes 1122, which allows fluid flow between the adapter 1110 and the vaporizer. Preferably, the sealing membrane 1120 is configured to receive the central pin 1132 and form a fluid seal therewith, such that flow through the central pin 1132 is substantially separated from flow through the through holes 1122 and 1128.

In one embodiment, illustrated in FIG. 27B, the disk 1124 is sufficiently sized to form a fluid seal with the fluid port 1130. This may be preferred because it prevents fluid leakage and may also be adapted to allow the fluid port 1130 to grip the disk 1124 while the container 1114 is rotated by a user to rotate the associated spout 1116 and bring it into an open position. If the disk is intended to form a fluid seal with the fluid port, then it may be surrounded by an o-ring or other elastomeric or deformable member, not illustrated, or it may itself be substantially comprised of an elastomeric or deformable material.

In another embodiment, the valve disk may be biased to the closed position in order to further avoid leakage during handling. This may be accomplished by any of a number of means, such as a torsion spring that must be overcome to align the disk through holes with the spout through holes.

A tactile, visual, or audible indicator may be provided to signal that the spout and disk are in an open position. For example, the disk may make a "clicking" noise when it is moved between closed and open positions. This is merely one possible indicating means and those of ordinary skill in the art will recognize that others are available and may be practiced with this aspect of the present invention.

It will be understood that the embodiments described above are illustrative of some of the applications of the principles of the present invention. Numerous modifications may be made by those skilled in the art without departing from the spirit and scope of the invention, including those combinations of features that are individually disclosed or claimed herein. For these reasons, the scope of the invention is not limited to the above description but is as set forth in the following claims.

The invention claimed is:

1. An adapter for establishing fluid communication between an anesthetic agent container and an anesthetic vaporizer having a fluid port and a vaporizer valve assembly with a central pin, the adapter comprising:
   a base mountable to the anesthetic agent container;
   a generally tubular spout extending away from the base;
   an adapter valve assembly for controlling fluid flow through the spout, the adapter valve assembly comprising a moveable tubular section having an inner flowpath; and
   a retainer associated with the adapter valve assembly and adapted for engagement with a central pin of an anesthetic vaporizer when at least a portion of the spout is inserted into the fluid port,
   the retainer comprising an annular gasket disposed in the inner flowpath of the tubular section.

2. The adapter of claim 1, further comprising an anesthetic agent container associated with the base and an amount of anesthetic agent housed within the container.

3. The adapter according to claim 1, wherein the annular gasket comprises an elastomer.

4. The adapter according to claim 1, wherein the adapter valve assembly comprising tapered sections adjacent to the retainer to guide the central pin into the retainer.

5. The adapter according to claim 1, wherein the spout has an open end and inwardly projecting teeth disposed about the open end of the spout.

6. The adapter according to claim 5, wherein the teeth are defined by discrete elements.

7. The adapter according to claim 1, wherein the spout and the adapter valve assembly define an outer flowpath therebetween.

* * * * *